(12) United States Patent
Searle et al.

(10) Patent No.: US 10,052,441 B2
(45) Date of Patent: Aug. 21, 2018

(54) SYSTEM AND METHOD FOR MEASURING DELIVERED DOSE

(71) Applicant: Becton, Dickinson and Company, Franklin Lakes, NJ (US)

(72) Inventors: Gary Searle, Norfolk, MA (US); Andrew Burke, Saunderstown, RI (US); Peter Costello, Raynham, MA (US); Kenneth Focht, Needham, MA (US); Francis L. Ross, Falls Church, VA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 205 days.

(21) Appl. No.: 15/226,638

(22) Filed: Aug. 2, 2016

(65) Prior Publication Data

US 2018/0036495 A1     Feb. 8, 2018

(51) Int. Cl.
*A61M 5/48* (2006.01)
*A61M 5/20* (2006.01)
*A61M 5/32* (2006.01)

(52) U.S. Cl.
CPC .............. *A61M 5/482* (2013.01); *A61M 5/20* (2013.01); *A61M 5/3286* (2013.01)

(58) Field of Classification Search
CPC .............. A61M 5/1411; A61M 5/1689; A61M 5/16804; A61M 5/16809; A61M 5/16813; A61M 5/16808; A61M 5/16822; A61M 5/16827; A61M 5/16895; A61M 5/482; A61M 5/20; A61M 5/3286
USPC ........................................... 604/67, 251, 186
See application file for complete search history.

(56) References Cited

U.S. PATENT DOCUMENTS

| 5,887,478 A | 3/1999 | Wang et al. |
| 2005/0199073 A1 | 9/2005 | Keech et al. |
| 2010/0305499 A1 | 12/2010 | Matsiev et al. |
| 2012/0103085 A1 | 5/2012 | Haartsen et al. |
| 2013/0237955 A1 | 9/2013 | Neta et al. |

FOREIGN PATENT DOCUMENTS

WO    WO-2016040949 A1    3/2016

*Primary Examiner* — Manuel Mendez
(74) *Attorney, Agent, or Firm* — Dickinson Wright, PLLC

(57) ABSTRACT

A flow sensor is provided to enable volumetric dose data to be acquired automatically by sampling flow rates of insulin measured by a flow sensor exposed to a flow manifold though which the insulin flows. The flow sensor preferably connects to a standard insulin pen on one end, and to a standard pen needle on the other end. Particular geometries and algorithms are utilized to accommodate the unique requirements of insulin flow determination during an injection event.

29 Claims, 28 Drawing Sheets

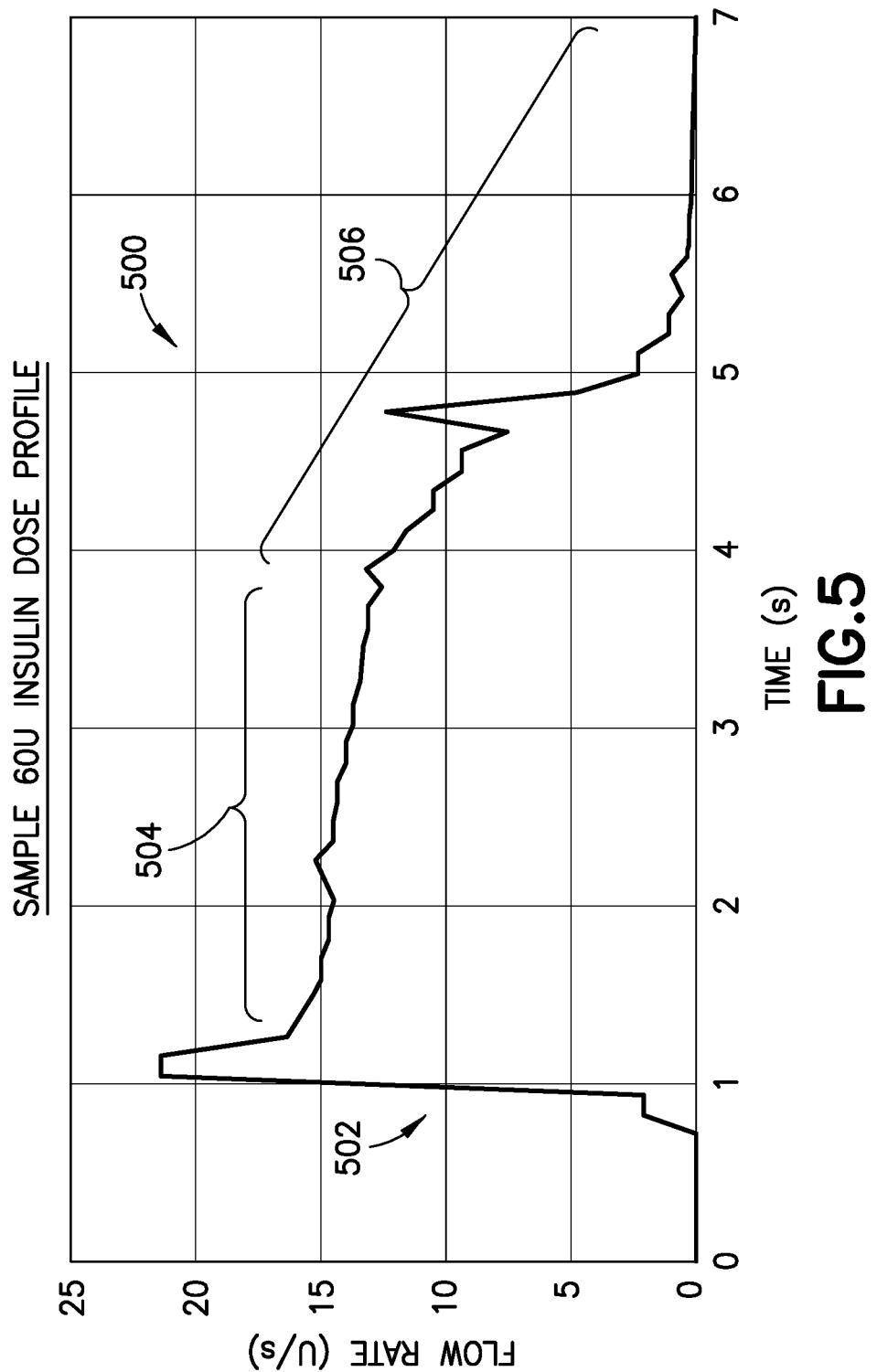

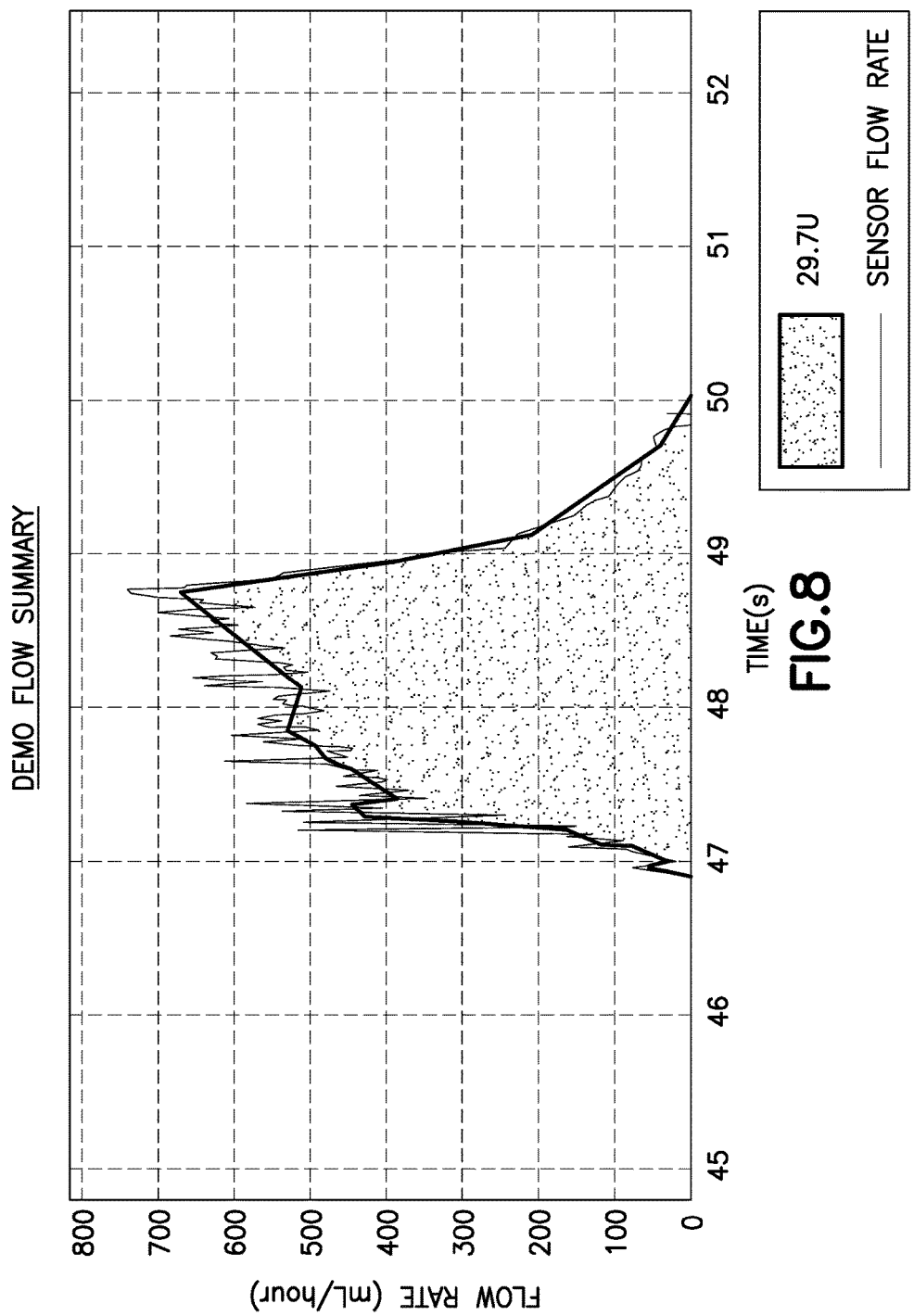

| HEAT-SENSOR SPACING | ΔPHASE: 200-1000ml/hr RANGE | ΔPHASE SHIFT RESOLUTION | ΔAMPLITUDE @ 1000ml/hr | HEAT-SENSOR SPACING % CHANGE FROM 150um |
|---|---|---|---|---|
| 130um | 1.236 | -15.2% | 0.2% | -13.3% |
| 200um | 1.976 | 35.5% | -23.1% | 33.3% |

FIG.14C

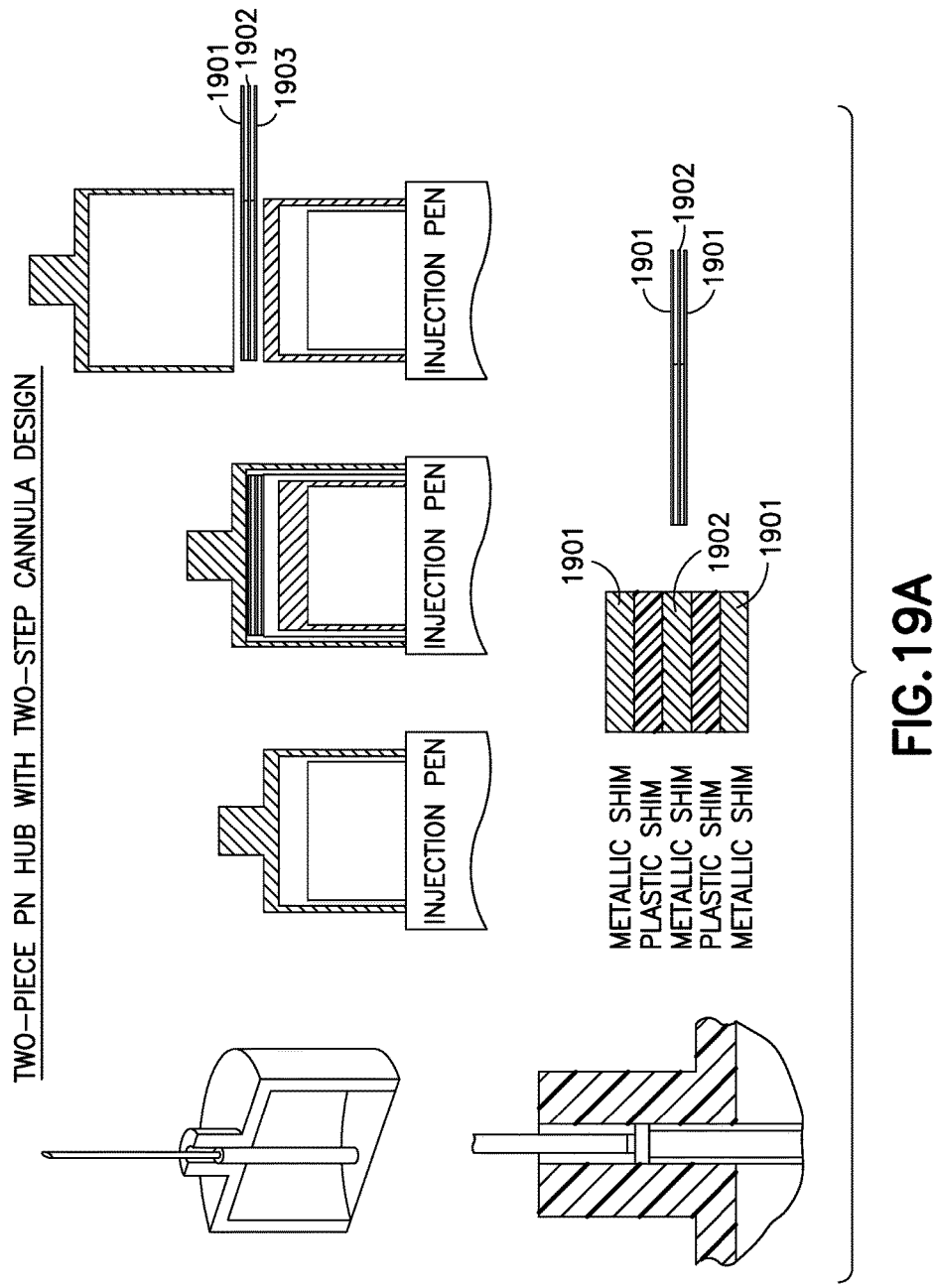

SYSTEM AND METHOD FOR MEASURING DELIVERED DOSE

FIELD OF THE INVENTION

The present invention relates to medication delivery devices. In particular, the present invention relates to systems and methods of measuring a dose delivered from an injection pen, or the like, utilizing a flow sensor.

BACKGROUND OF THE INVENTION

Dose measurement is an important component of any medicine therapy, and especially important for an insulin therapy regimen for diabetics. To properly manage their self-therapy and communicate their conformance to a prescribed regimen, diabetics are typically required to manually record insulin injections into a logbook. Recently, a few injection pens and pen attachments have been developed for the purpose of measuring and automatically data logging the dose delivered, e.g. motorized injection pens and attachments that approximate the position of a plunger within an insulin reservoir to determine how much insulin has been delivered. However, none of the current solutions are adequate. Manual recording of insulin doses is inherently inaccurate due to human errors and omissions, and measurement of a plunger, while an improvement over manual recording, is still not accurate enough for individual doses and does not record the time that doses are delivered.

Thermal time of flight (TTOF) sensors are used to detect the time of flight of a heat pulse induced into moving fluid as it travels through a channel of known cross-section over a known distance in order to measure volumetric flow of the fluid. However, existing TTOF sensors are typically used in steady state flow scenarios, and have not to date been required to measure rapid and large changes in flow rate, as is expected in an insulin injection from an insulin pen, or the like.

There are three operating modes for a thermal flow sensor: anemometric, calorimetric and thermal time of flight (TTOF). The simplest type of thermal flow sensor is the so-called hot wire anemometer. L. V. King conducted the first systematic investigation of the hot wire anemometer in 1914, which yielded King's Law, describing the heat transfer from a cylinder of infinite length. The hot wire anemometer is simply a platinum wire inserted into a fluid flow using either a constant current or constant temperature mode of operation. Commercial thermal dispersion mass flow meters, based on constant temperature hot wire anemometry, emerged by the 1960s for industrial mass flow measurement of gases in pipes and ducts. Also in the 1960s, the capillary mass flow meter (as part of a mass flow controller) emerged to provide mass flow control at relatively low flow rates for gases in the semiconductor industry. This device uses a capillary sensor tube and a bypass, operating in calorimetric mode, by placing two platinum RTD (resistance temperature detector) windings around the capillary, which each serve as both sensor and heater. Calorimetric flow sensing has a linear relationship between the voltage output and the flow rate, but only at low flow velocities, which is the reason for the bypass configuration of the capillary based mass flow controllers. All three thermal flow sensing modes can also be applied in a MEMS-based fluid flow sensor where microfabrication is used to miniaturize and potentially mass-produce the sensor at low cost. In exemplary embodiments of the invention described herein, thin film structures serve as the heating elements and sensors. MEMS sensors also enable significant reduction of required power input. Anemometric flow sensors do not exhibit good accuracy at lower flow rates, so it is not a preferred mode for MEMS based sensors. The first MEMS thermal flow sensors (anemometric) emerged in the mid-1970s and by the 1980s it had become an active area of academic research with the first commercial thermal (calorimetric mode) MEMS airflow sensors appearing toward the end of the 1980s. MEMS flow sensors are also being adopted for mass flow controllers in place of the conventional capillary tube configuration. The design of a calorimetric MEMS sensor chip is usually a symmetrical layout on a substrate with an upstream and downstream sensor element on either side of a heating element with separation ranging from the 10s to 100s of microns. The same layout can also be used for a TTOF sensor, although utilizing the upstream sensor is not necessary unless the flow is bi-directional. Commercial MEMS thermal flow sensors are generally calorimetric, so in order to measure higher flow rates they have to be configured to operate with a bypass or increase the internal flow tube's diameter to reduce the flow velocity. The latter negatively impacts the accuracy and effective response time of the sensor. Calorimetric MEMS sensors work well for relatively low, steady-state flow conditions, such as infusion for liquid flow sensing, but do not have the accuracy, sensitivity, dynamic range, and response time necessary to accurately measure the volume of highly transient flow conditions of insulin injections. Conventional calorimetric (and TTOF) MEMS sensors that utilize a membrane as substrate cannot withstand the elevated pressure of insulin injections. TTOF sensing directly measures the velocity of the streaming fluid and therefore the volume of fluid rather than the mass flow of calorimetric (and anemometric) sensing. Microfabrication enables a TTOF sensor to attain greater accuracy because it enables submicron precision of the separation between the heating and sensing elements. Volumetric measuring is advantageous for some applications, inasmuch it is not necessary to calibrate the sensor for a specific fluid. TTOF sensing can also accurately measure flow at the much higher transient velocities of insulin injections, unlike calorimetric sensing. However, TTOF sensing is susceptible to error at very low flow rates due to thermal diffusivity in the fluid and detects a lot of noise at zero flow. Therefore, conventional TTOF sensing is not useful for detecting the onset of flow, which is very important for flow sensing over the relatively short duration of an insulin injection. Therefore, an ideal thermal flow sensor for insulin injection is a MEMS based device that is designed to operate in calorimetric mode at the onset of flow and then instantly switching to TTOF mode at a pre-selected flow rate. This type of sensor can be described as a hybrid TTOF sensor. Exemplary embodiments of the present invention, as will be described in further detail below, are designed to leverage the advantages of MEMS fabrication technology and hybrid TTOF mode operation; this results in a custom liquid volume sensor that meets the unique requirements for flow sensing during insulin injections.

Existing TTOF sensors are inadequate for sensing delivered doses of insulin injections because they lack the ability to measure the full range of flow rates typical of insulin injection, to respond instantaneously at the onset of a dosing event, and the ability to measure highly variable flow rates. In addition, conventional TTOF sensors are unable to handle the pressures associated with fluid injection devices such as syringes and pen needles.

Accordingly, there is a need for a flow sensor with a rapid sensor response time, in order to detect the transition from a zero flow state to a minimally detectable velocity. Further, there is a need for flow sensor that performs accurately from near zero flow condition and throughout the full range of flow velocities to be expected during an injection, since the velocity of fluid flow during an injection is transient during the majority of the injection cycle. There is also a need for a TTOF sensor that does not impart too much heat to the flowing insulin, since excess heat can denature or otherwise detrimentally affect the medicinal effect of the insulin. Throughout this specification, reference is made to insulin flow. However, it should be appreciated by those of ordinary skill in the art that embodiments of the invention described herein could be utilized with many medications or other fluids, and insulin should be understood to be exemplary.

SUMMARY OF THE INVENTION

The above described disadvantages are overcome and other advantages are realized by embodiments of the present invention, as will be appreciated by those of ordinary skill in the art. Exemplary embodiments provide an accurate and reliable TTOF sensor for insulin dosing. Unique sensing chip structures are described herein, together with customized electronic drive and measurement circuits, dose volume calculation algorithms, and flow path and manifold geometry. In particular, embodiments of the invention utilize both amplitude and phase signals received at sensing elements upstream and downstream of a heating element to identify the start of fluid flow, and to periodically measure the flow rate. The result is a sensing system with response time, dynamic range, and accuracy tailored to the requirements of insulin delivery, and exceeding the typical standards for commercially available flow sensors.

BRIEF DESCRIPTION OF THE DRAWINGS

The invention will be more readily understood with reference to the embodiments thereof illustrated in the attached drawing figures, in which:

FIG. 5 illustrates a typical insulin dose profile measured by a device according to an exemplary embodiment of the invention;

FIG. 8 illustrates a sum of trapezoids method of integrating flow readings to calculate a dose volume according to an exemplary embodiment of the invention;

FIGS. 14A-14C illustrate polar calibration plots and a summary table for a sensor device according to an exemplary embodiment of the invention;

FIGS. 19A-19B illustrate a segmented cannula sensor according to another exemplary embodiment of the invention.

Throughout the drawings, like reference number should be understood to refer to like elements, features and structures.

DETAILED DESCRIPTION OF THE EXEMPLARY EMBODIMENTS

Figure 1:
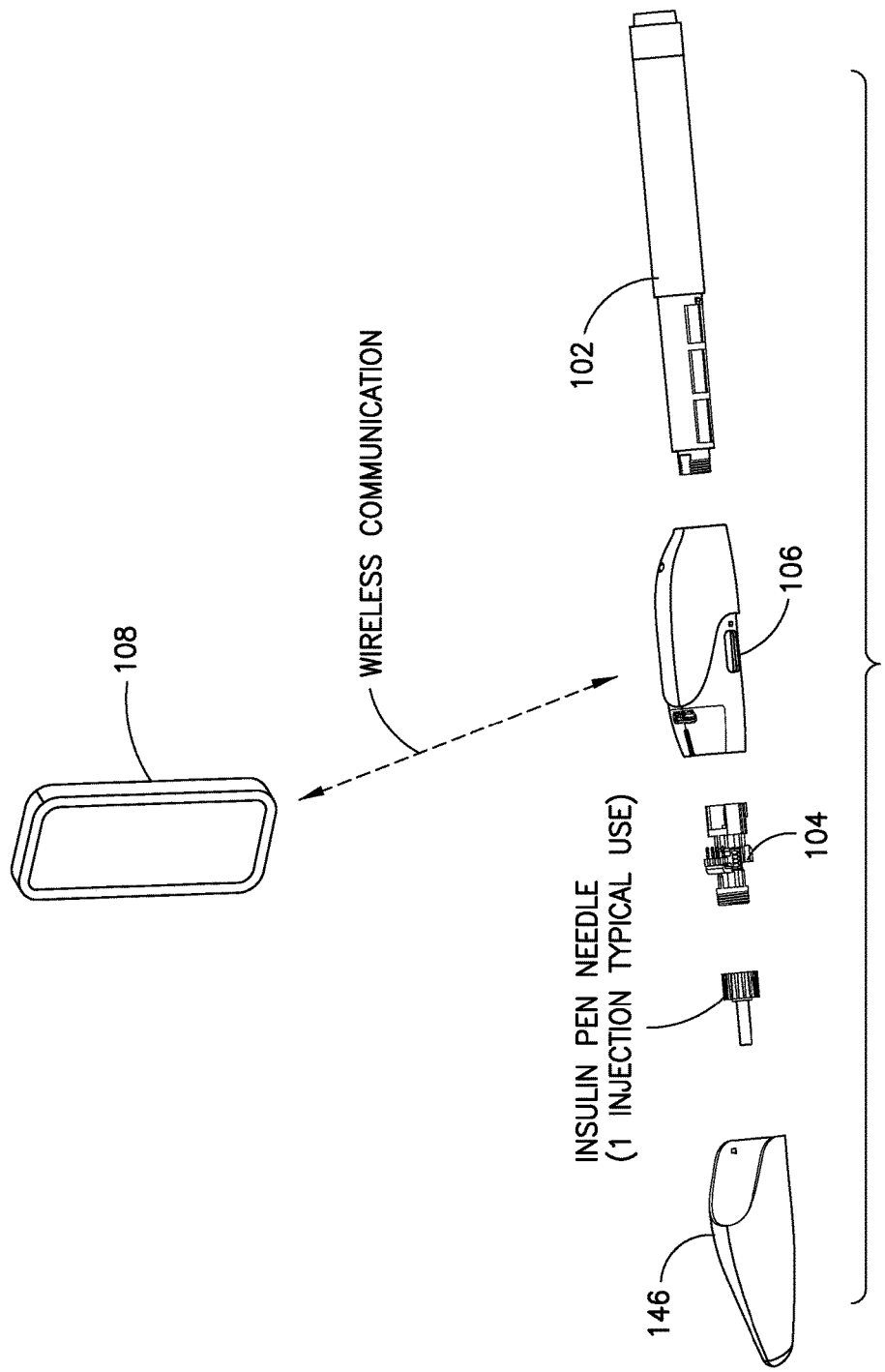
FIG. 1 illustrates a dose capture system according to an exemplary embodiment of the present invention.

The exemplary embodiments of the invention will now be described with reference to the attached drawing figures. FIG. 1 illustrates an exemplary dose capture system 100 that preferably integrates with a conventional insulin pen 102. While this exemplary embodiment is illustrated in connection with an insulin pen, it should be appreciated that embodiments of the invention may be utilized with any suitable medication device, including without limitation, patch pumps, IV pumps, fixed dose injectors, auto injectors, syringes, and so on. The system 100 comprises a semi-disposable flow sensor 104 that includes a fluid manifold and a Thermal Time of Flight (TTOF) hybrid sensor. The semi-disposable flow sensor 104 preferably has a life equivalent to the insulin pen 102 to which it is attached. The system 100 further comprises a durable portion 106, which preferably has a multi-year lifespan. The durable portion 106 consists of a plastic enclosure containing electronics that power the flow sensor and read the sensor signals, a microprocessor for analyzing dose data, re-chargeable battery, temperature and motion and/or position sensors, and wireless communication circuitry. The durable portion 106 also preferably has removable cap 146 that can provide one or more of the following functions: protects the semi-disposable flow sensor, shields the insulin from light, protects the patient from unintended needle stick, and acts as a switch for an electrical contact closure that activates and deactivates the sensing system, when the cap 146 is removed from or replaced onto the durable, respectively. The durable portion 106 preferably is adapted to be charged via a standard connector such as a USB port, or preferably, via a wireless charging system. Preferably, a smart phone 108 based software application interacts wirelessly with the durable portion 106 to read, store, and present dose information. The application can also interact with other electronic devices and networks, such as glucose meters, activity & fitness meters, or diabetes care networks. The software application is preferably paired with the durable portion 106 one time. After the initial pairing, the software automatically recognizes the durable portion 106 and is capable of securely transferring data from the durable portion 106 to the smart phone application automatically. It should be appreciated that in alternate embodiments of the invention, other pairing arrangements could be made as appropriate and desired.

The semi-disposable flow sensor 104 preferably has a threaded portion 114 to receive a standard insulin pen needle 110. The pen needle is preferably changed with each insulin dose as is conventional.

Figure 2:
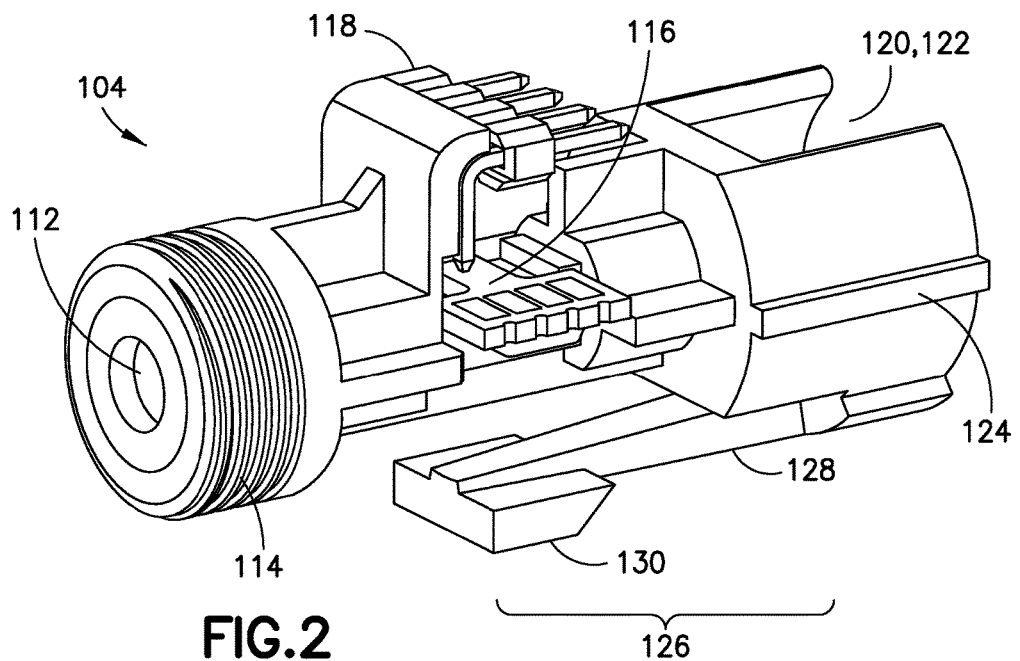
FIG. 2 illustrates a semi-disposable portion of the dose measuring system of FIG. 1.

The semi-disposable flow sensor 104 is described in further detail in connection with FIG. 2. As illustrated a distal end of the semi-disposable flow sensor 104 comprises a septum 112 and a universal pen needle thread 114. A MEMS flow sensor chip 116 is mounted on a carrier printed circuit board, and fixed to the semi-disposable flow sensor assembly 104. An electrical connector 118 is provided for making electrical connections between the semi-disposable flow sensor portion 104 and the durable portion 106. A proximal end of the semi-disposable flow sensor portion 104 comprises an insulin pen connection 120 with an inlet cannula 122. The semi-disposable 104 preferably also includes alignment features 124 on the housing to align the semi-disposable 104 within the durable portion 106. The semi-disposable preferably includes an axial lock 126, or similar feature, to releasably lock the semi-disposable 104 within the durable portion 106. As shown, the axial lock 126 comprises a flexible member 128 and a locking member 130 adapted to be locked into a corresponding feature of the durable portion 106.

Figure 3:
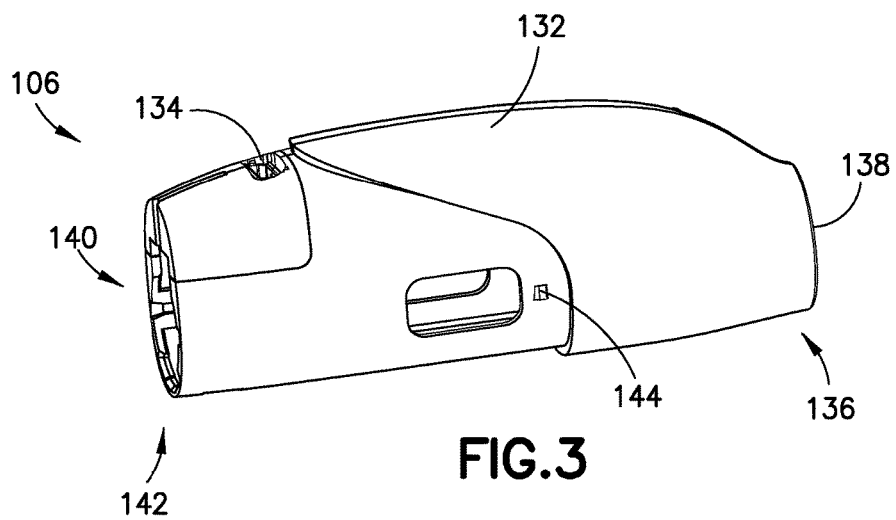
FIG. 3 illustrates a durable portion of the dose measuring system of FIG. 1.
Figure 20:
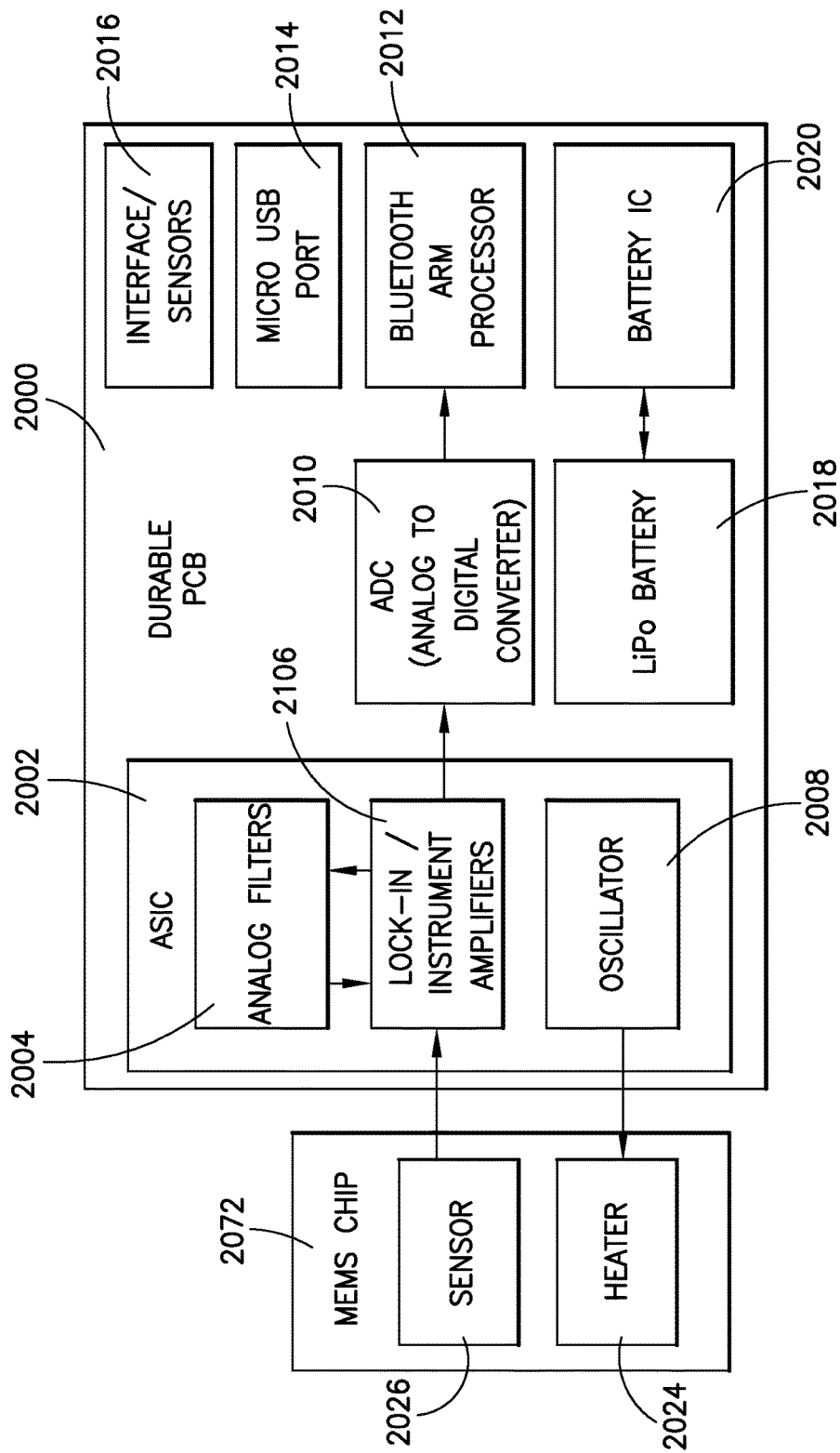
FIG. 20 illustrates a block diagram of a circuit board according to an exemplary embodiment of the invention.

The durable portion 106 will now be described in further detail with reference to FIGS. 3 and 20. As illustrated, the durable portion 106 comprises an outer housing 132 that preferably includes an opening for a charging port 134. The charging port 134 preferably conforms to a regularly adopted standard such as mini-USB, or the like, although any suitable connection may be utilized, including a proprietary connection. Alternately, a wireless charging arrangement can be incorporated into the durable unit. The durable unit has a proximal end 136 that includes an opening 138 for attachment to an insulin pen 102. The durable unit further has a distal end 140 that includes an opening 142 adapted to receive the semi-disposable portion 104. The durable portion 106 preferably is contoured and includes detents 144, or similar features, to receive a removable cap 146. The durable portion 106 includes a printed circuit board 2000, illustrated in FIG. 20. The durable PCB 2000 preferably includes an ASIC 2002, that provides analog filters 2004, lock-in/instrument amplifiers 2006, and an oscillator 2008. The ASIC 2002 provides data to an analog to digital converter (ADC) 2010. The ADC 2010 in turn provides data to a Bluetooth ARM processor 2012. The durable PCB 2000 further includes a communications port 2014 such as a micro-USB port, interface/sensors 2016, and battery components 2018/2020. The durable PCB 2000 interfaces with the MEMS chip 2022 that provides the heater 2024, and sensor elements 2026.

Now operation of the dose capture system according to an exemplary embodiment will be described. The dose capture system 100 is installed on an insulin pen 102 as part of the set up sequence with each new pen, that is, every three (3) to seven (7) days (nominally five (5)) for a typical user. The durable portion 106 is first attached to the insulin pen 102. The semi-disposable 104 is then inserted into the distal opening 140 of the durable portion 106. Cannula 122 of the disposable portion 104 pierces the distal septum of the insulin pen 102, creating a flow path over the TTOF sensing element. As the semi-disposable portion 104 is inserted into the durable portion 106, electrical connector 118 is mated with a corresponding electrical connector within the durable portion 106, creating electrical connections to the TTOF sensor 116. A pen needle is threaded onto the distal threaded end 114 if the disposable portion 104, such that the pen needle cannula pierces the septum 112, completing a fluid path from the insulin pen through the flow sensor and pen needle. The combined insulin pen and dose sensing system is then primed in the normal manner to remove trapped air.

Although in this embodiment the assembly sequence is durable portion 106 first and semi-disposable portion 104 second, the system can be designed with the assembly order reversed, as will be appreciated by those of ordinary skill in the art. With this assembly sequence, the durable portion 106 could be used on different insulin pens, such as one pen with slow acting insulin and a second pen with fast acting insulin. The semi-disposable portion 104 preferably attaches to the universal ISO connection found on each insulin pen, and the durable portion 106 would then attach to the semi-disposable portion 104 and to the body of the insulin pen. Since the durable portion 106 does not contact insulin, the durable portion 106 is capable of being swapped back and forth between multiple pens as required for the user's therapy without affecting the sterility of the insulin. For therapy involving more than one insulin or drug, a means of recognizing the additional drug to which the durable attached is provided. For example. a camera on the smart phone that is paired with the durable portion is used to read a bar code on the injection pen when the durable unit is attached to the pen.

The durable portion 106 is preferably paired with the smart phone application, as discussed above. A pairing procedure is preferably done once for a given cell phone 108/durable portion 106 pair. After the initial pairing, the cell phone 108 application preferably automatically recognizes and communication with the paired durable portion 106.

Once installed on the insulin pen, the exemplary system automatically recognizes and captures dose events as part of the user's normal injection sequence. Preferably, no additional use steps beyond those necessary for a normal insulin pen injection are required for the dose sensor after the initial set up on the pen. Dose volumes and times are calculated by the durable portion 106. The durable portion 106 preferably can store many insulin pens worth of dose data. Data recorded by the durable portion 106 is preferably transferred to the smart phone 108 application whenever the smart phone 108 and the durable portion 106 are within broadcast range of one another. The dose data transferred to the smart phone 108 is preferably presented to the user in a convenient and easy to read format. Dose information may also be transferred from the cell phone to other diabetes management devices or to a cloud based data storage site if desired for further processing and analysis and transfer to other stakeholders in the patient's healthcare network.

When the insulin pen 102 is empty, the durable portion 106 is removed and readied for the next use. The spent insulin pen 102 and the semi-disposable portion 104 combination are discarded in the same way as conventional diabetes pens. The durable portion 106 or the semi-disposable portion 104 preferably have features to prevent the reuse of a semi-disposable portion 104 on another insulin pen 102.

Figures 4A, 4B, 4C:
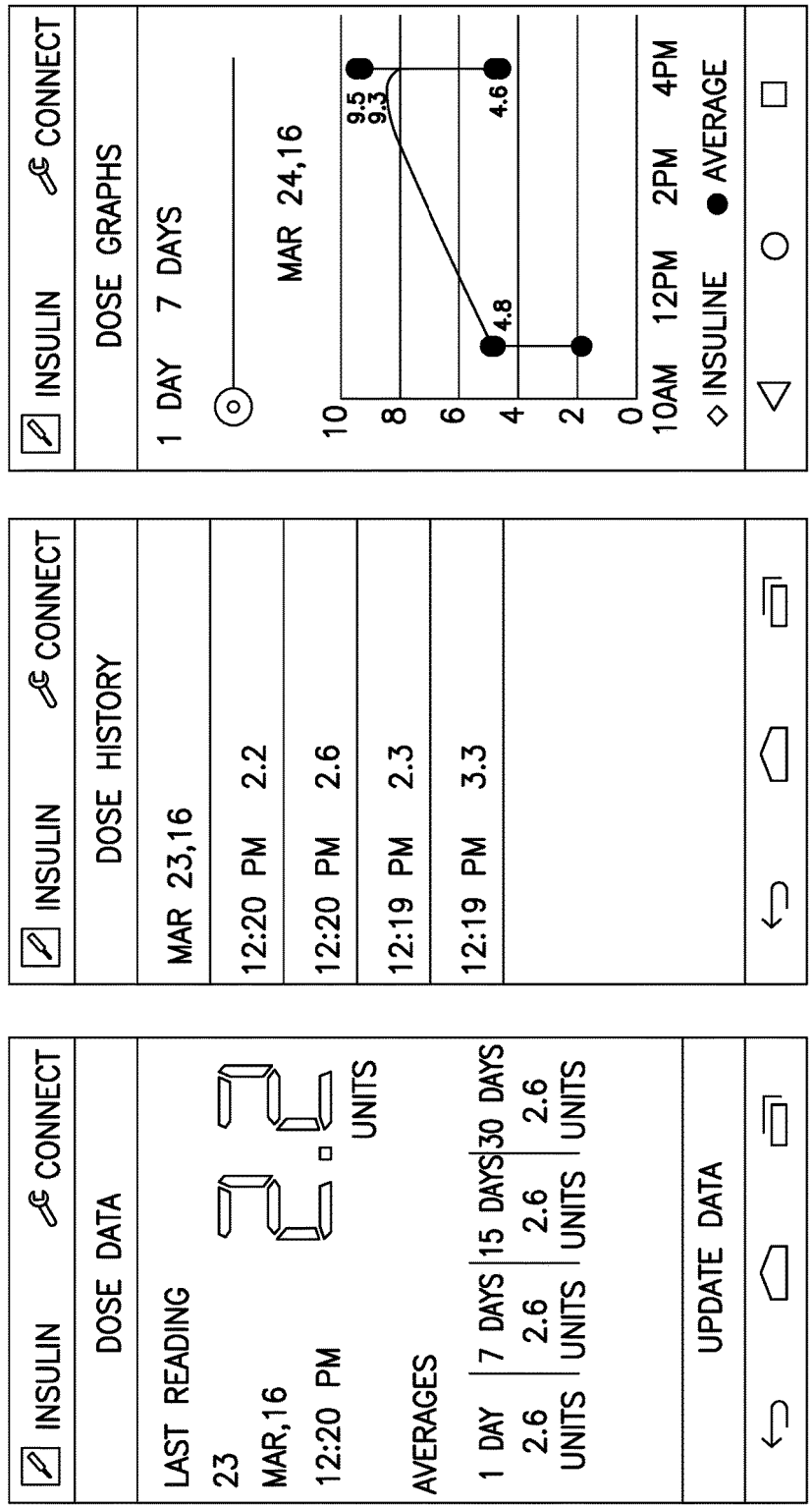
FIGS. 4A-4C illustrate exemplary interface screens of a cell phone application according to an exemplary embodiment of the invention.

Next we describe an exemplary smart phone 108 application. The smart phone application preferably displays dose data to the user in an easy to understand format. FIG. 4A shows a dose overview window, where recent dose measurements and time based averages can be shown. FIG. 4B has a dose log that can be reviewed by the user for accuracy and also provides a location for notes and other context based data. FIG. 4C shows a graph of dose measurements over selectable time ranges, which can provide trend insights to the user.

Several aspects of insulin injection present significant challenges to measuring accurate doses. Insulin dose size can vary greatly, from as low as 3.3 microliters to as high as 800 microliters. Dose delivery times can vary from less than 1 second to greater than 10 seconds based upon the size of the dose, diameter and length of the needle being used, the friction and mechanical efficiency of the insulin pen, and actuation force applied by the user or the spring loaded actuation of the pen. A typical insulin injection flow profile 500 is shown in FIG. 5. The flow profile has a sudden, large increase in flow at the beginning of the injection 502, a continuously varying flowrate 504, and relatively long flow decay 506 at the end of the dose. In order to calculate an accurate dose, the flow sensor must respond quickly and accurately to all portions of the flow profile. The flow sensor must be able to respond to the abrupt changes in flow and must be accurate over the range of flowrates that could be produced by a wide range of users. Advantageously, embodiments of the present invention are capable of determining a dose amount by integrating flow rate measurements over time. Alternately, several flow rate data points or an overall shape of the flow curve may be matched to a stored table of dose values, such as incremental doses from 1 unit to 60 units, for example International standards currently require volumetric accuracy equivalent to the minimum resolution of the insulin pen or +/−5% of the dose volume, whichever is greater. For example, on the typical U-100 pen with a dial resolution of 1 U, accuracy of +/−10 microliters for doses less than 200 microliters and +/−5% for doses greater than 200 microliters is required. Higher insulin concentrations scale inversely with respect to volume. For instance, a U200 insulin pen with resolution of 1 U would require volumetric accuracy of +/−5 microliters for doses less than 100 microliters and +/−2.5% for doses greater than 100 microliters.

Small diameter needles are typically used for insulin injections which can create relatively high back pressures. Accordingly, a flow sensor according to an embodiment of the invention must be able to tolerate back pressures of up to 1 mega-pascal.

Since the flow sensor is in the insulin delivery path, it must be manufactured from materials that are chemically compatible with the insulin, and must not in any way react with or break down the insulin.

Figure 6:
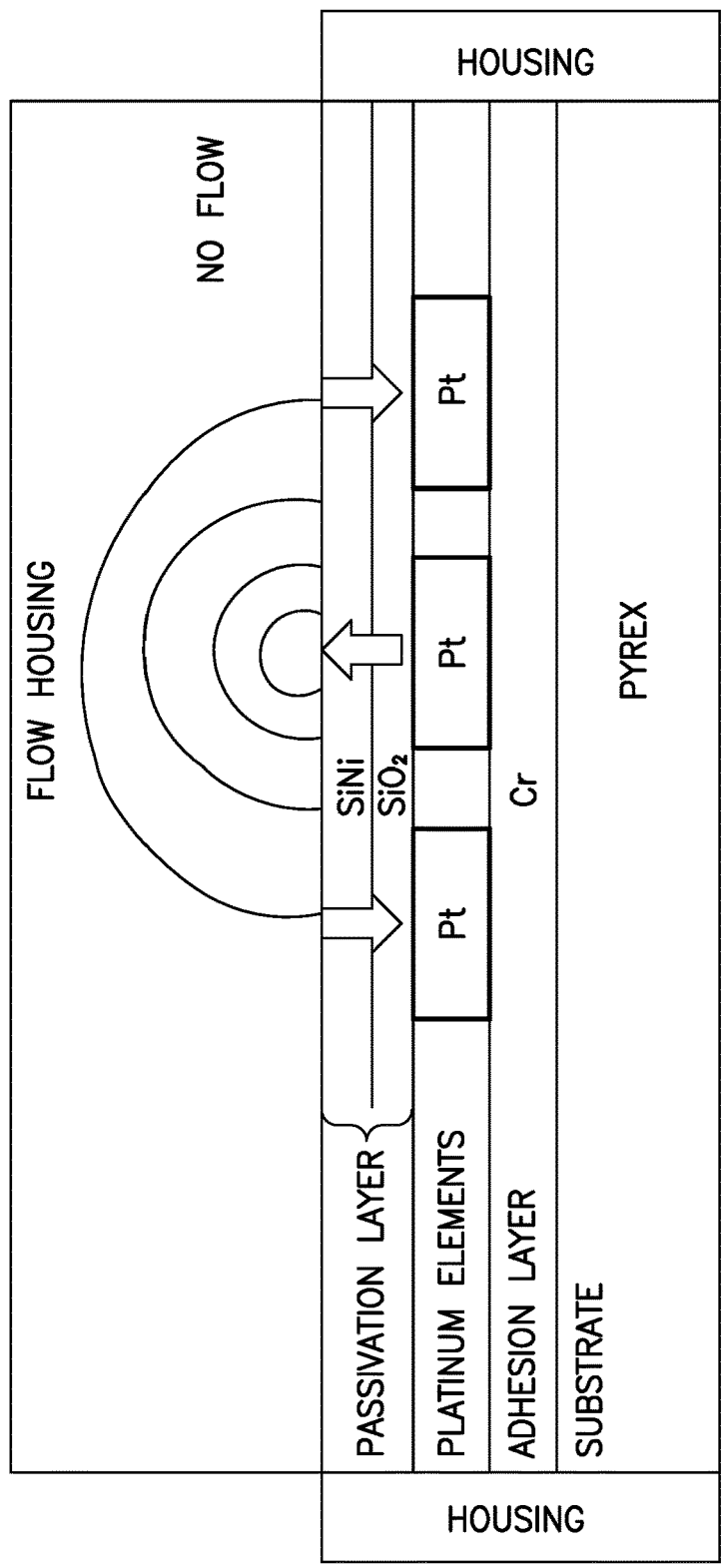
FIG. 6 illustrates a cross section of a thermal field in a sensor when fluid is not flowing.
Figure 7:
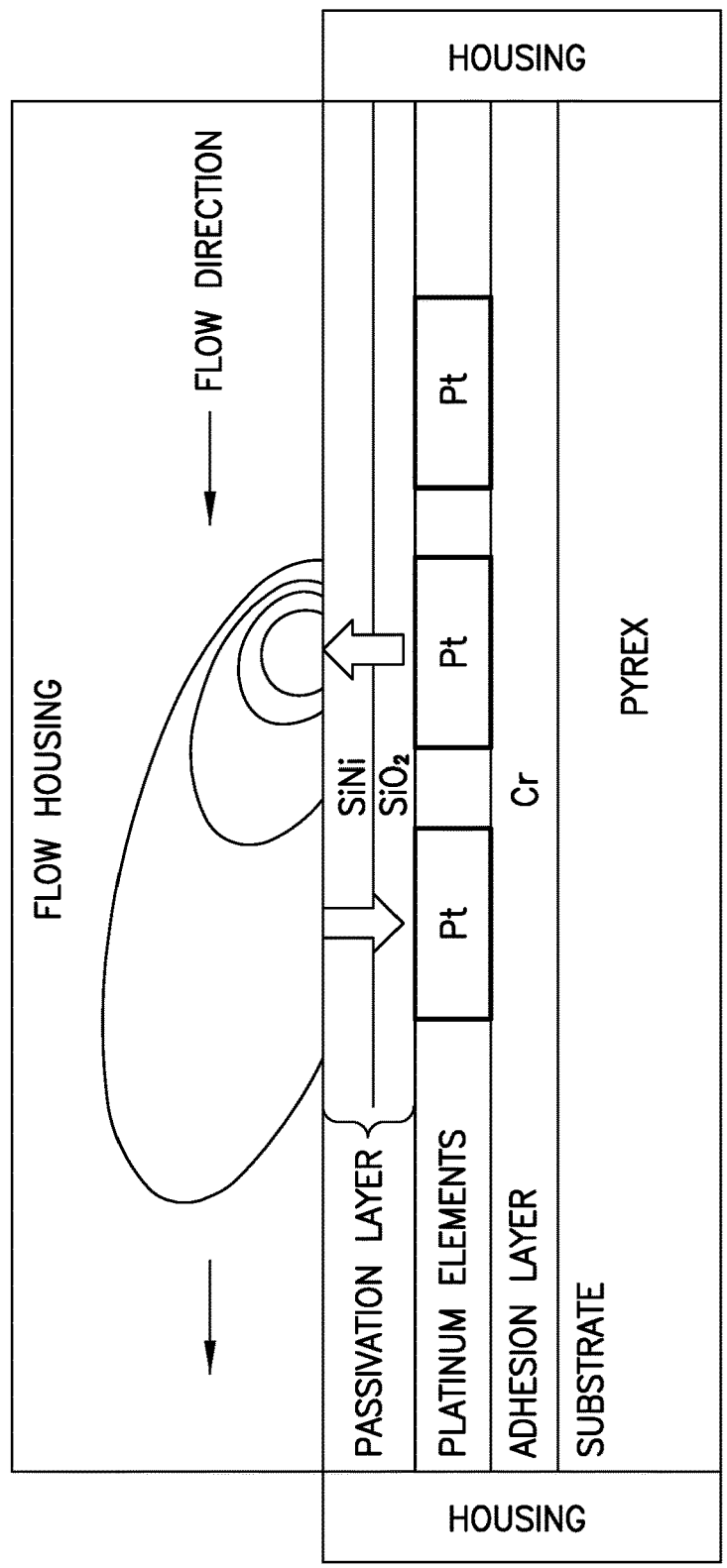
FIG. 7 illustrates a cross section of a distorted thermal field in a sensor with fluid flowing.

According to exemplary embodiments of the invention, TTOF flow sensing uses a central heating element with offset thermal sensing elements. The offset of each sensing element is preferably, but not necessarily, symmetrical on either side of the heating element. A time varying signal of known amplitude, frequency, shape and phase is applied to the central heater. The heat signal diffuses through the fluid toward the sensors, where it is detected with both reduced amplitude and a shifted phase relative to the drive signal. The amplitude signal corresponds to calorimetric sensing while the phase shift signal corresponds to time of flight sensing. Without flow, the thermal conduction zone around the heater is symmetric, as shown in FIG. 6. The electronics in the durable portion 106 senses balanced signals from the upstream and downstream sensors. The common signal seen by both sensors if filtered out by the electronics and the electronics calculates a no-flow condition for the sensor. With flow, the thermal zone is distorted by fluid convection, as shown in FIG. 7. The thermal signal is unbalanced, and the electronic signal seen on the downstream sensing element is shifted in phase (time) and amplitude relative to the input and relative to the upstream sensor. Advantageously, sensor signals from both upstream and downstream sensor traces are sampled throughout the flow range expected during an injection event. The shift in sensor signals is read by the durable portion 106 electronics and converted into an instantaneous flowrate of insulin by referencing a stored calibration curve or table. By sampling the instantaneous flowrate at precise and frequent time intervals, the total volume delivered can be calculated for each dose event. FIG. 8 illustrates an exemplary dose event, and the related data captured by the flow sensor to calculate the volume of the dose.

Several dose tracking insulin pens are currently available on the market. These pens track and monitor the motion of the pen mechanism to determine the dose delivered. Conventional pens use a small display to communicate intended dose volume of recent injections. Some newer models also incorporate wireless communication to a smart phone. Tracking the pen injection mechanism can fail to correctly monitor dose received by the user, as the pen mechanization has inherent error, which can be additive to the error in the sensing apparatus. Additionally, user errors, such as withdrawing the pen from the injection site before the dose is completely delivered into the tissue or not recognizing failures with system components, e.g. a pinched or clogged pen needle, can all contribute to not delivering the intended dose. Unlike conventional insulin pens, exemplary embodiments of the invention utilize TTOF sensing to measure the time and changing insulin flowrate profile actually delivered from the pen, allowing for more complete and accurate information on the actual dose delivered.

Thermal MEMS flow sensors are used in commercial applications due to their small size and accuracy. Micro Electromechanical Systems (MEMS) technology allows for the fabrication of micrometer scale heating and sensing elements with precise feature tolerances, resulting in sensors with minimal heat input to the fluid and highly accurate sensor features. However, commercially available thermal MEMS flow sensors are typically used in gas applications in steady state modes to measure mass flow rates over a relatively narrow range. Sensors that are readily available on the market, however, do not have the accuracy, sensitivity, dynamic range, ability to withstand injection pressures, and response time necessary to effectively measure highly transient insulin doses. Exemplary embodiments of the present invention are designed to leverage the advantages of TTOF fabrication technology, but result in a custom liquid volume sensor that meets unique requirements and needs for insulin injection.

Figure 9A:
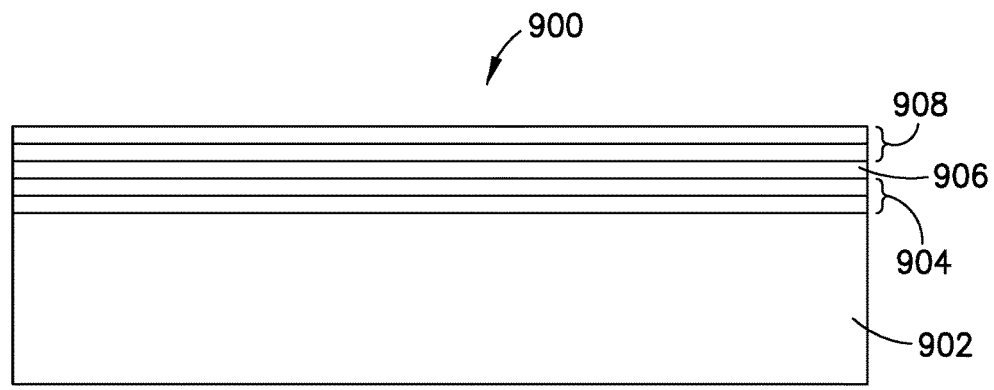
FIG. 9A-9B illustrates a cross section of a sensor chip according to an exemplary embodiment of the invention.
Figure 9B:
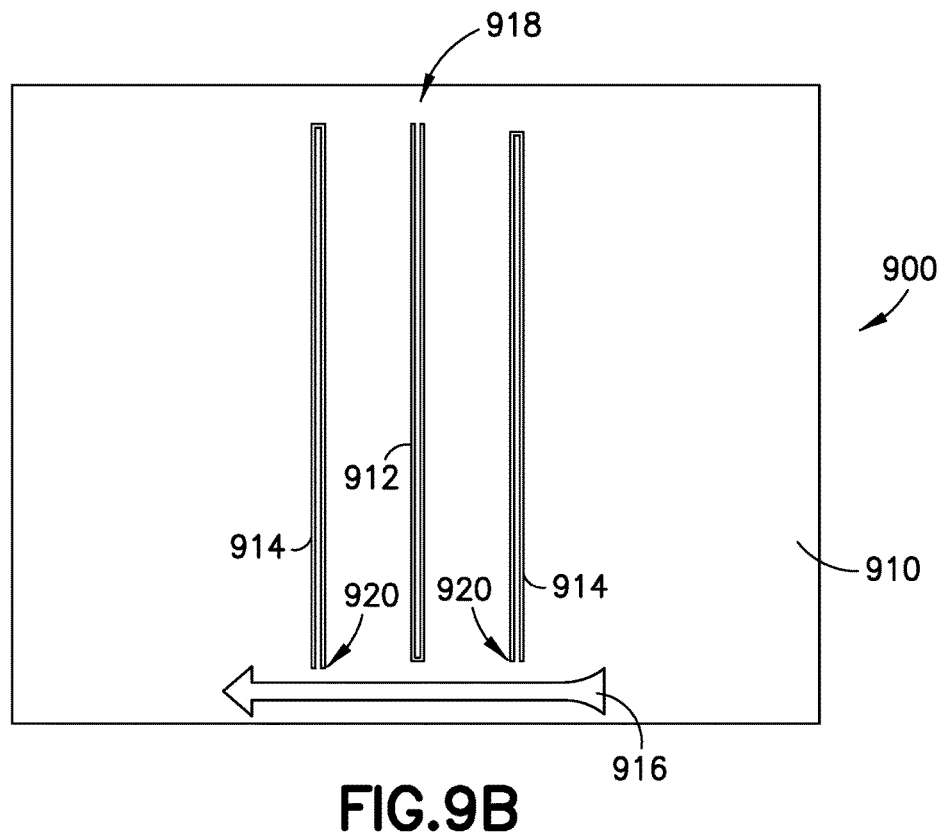
Figure 10:
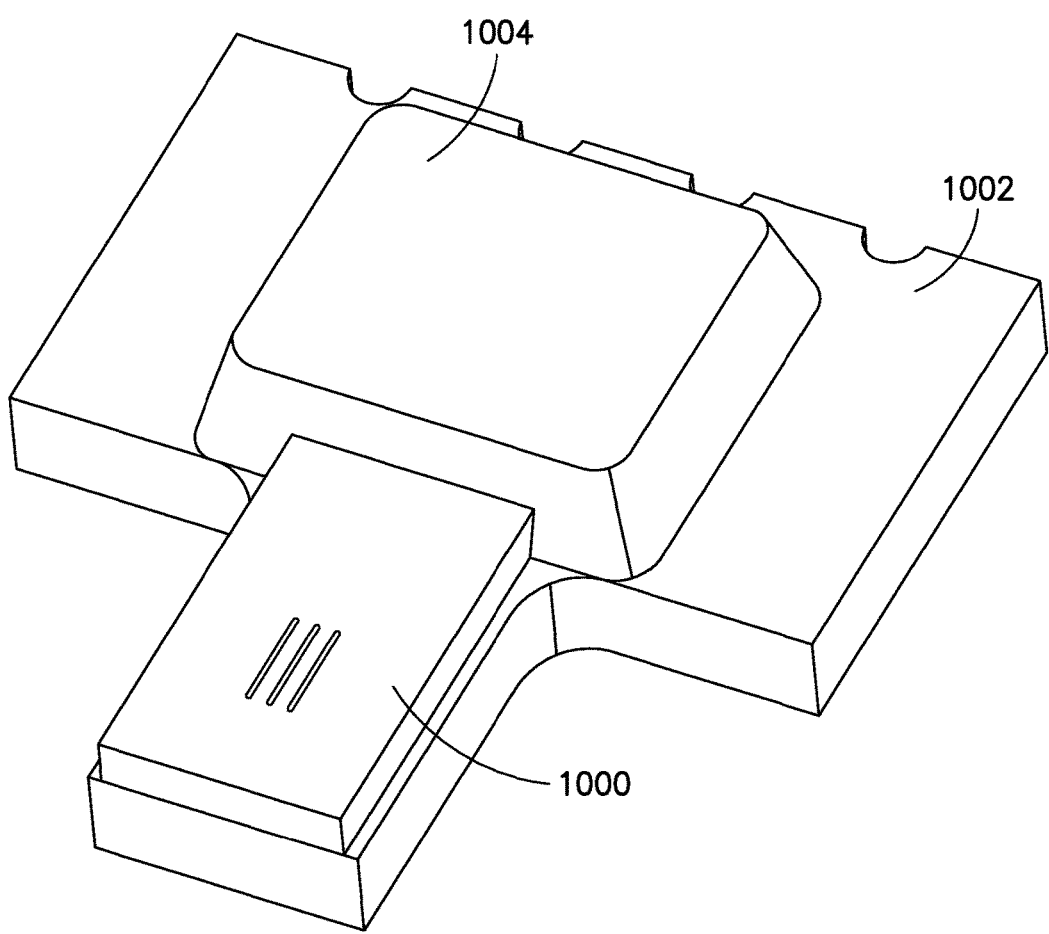
FIG. 10 illustrates a sensor chip mounted onto a carrier PCB according to an exemplary embodiment of the invention.

A method of manufacture of the sensing chip will now be described with reference to FIGS. 9A and 9B. As illustrated in FIG. 9A, which is a cross section of the sensing chip, the liquid flow sensing chip 900 is manufactured by sequentially depositing layers of material onto a substrate 902. Photomasks are used to pattern the layers using plasma or wet etching, or liftoff for precious metal layers. The layers include an adhesion layer 904, and element layer 906, and at least one passivation layer 908. After the deposition sequence, the substrate 902 is cut into individual sensor chips, which are then mechanically mounted to a printed circuit board and wire bonded for electrical connections. FIG. 9B illustrates a sensor face 910 of the sensor 900. As illustrated, the element layer 906 is exposed on the sensor face 910 to form a heating element 912 and two sensing elements 914. The heating 912 and sensing 914 elements are preferably long from end to end, but as narrow as possible in the width direction 916 (insulin flow direction). As shown, the heating 912 and sensing 914 elements are formed as long u-shaped traces such that the respective ends of each element are close together for convenient electrical connection. Accordingly, each of the heating 912 and sensing 914 elements is relatively long and narrow, with electrical connections located for convenient electrical attachment. As shown, the heating element 912 is oriented with electrical connections 918 on one side of the sensor face 910, while the sensing elements 914 are oriented in the opposite direction with electrical connections 920 on the other side of the sensor face. FIG. 10 illustrates an individual sensing chip 1000 mounted to a printed circuit board 1002, and having a wire bond area 1004 for the electrical connections.

As described herein, several aspects of the thermal MEMS flow sensor construction according to exemplary embodiments of the invention enable the performance required for insulin dose sensing.

Figure 11A:
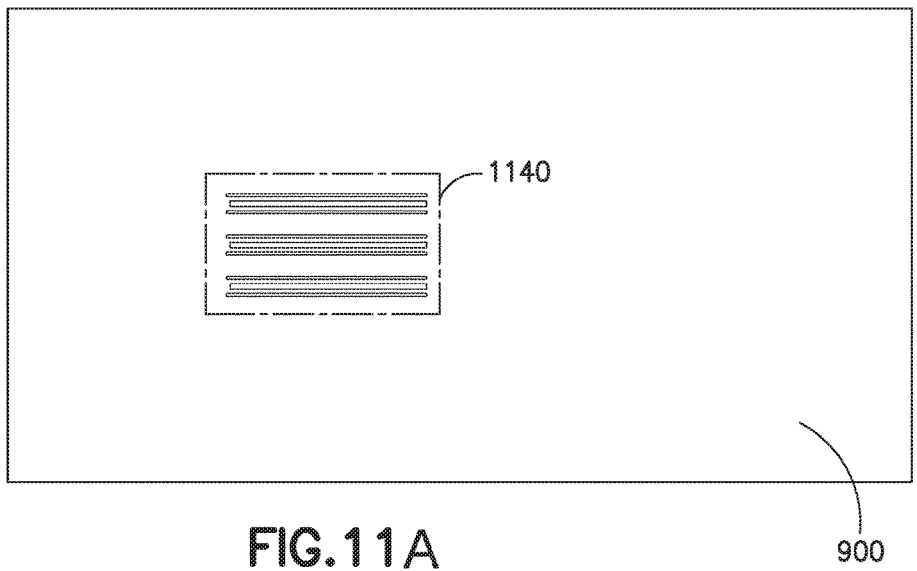
FIG. 11A-11D illustrate back etching and conductive break features of a sensor chip according to an exemplary embodiment of the invention.
Figure 11B:
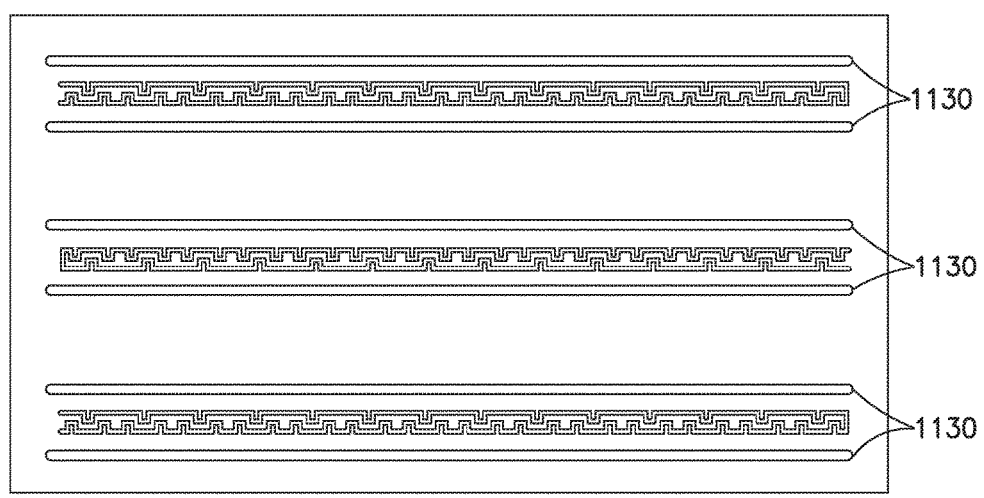
Figure 11C:
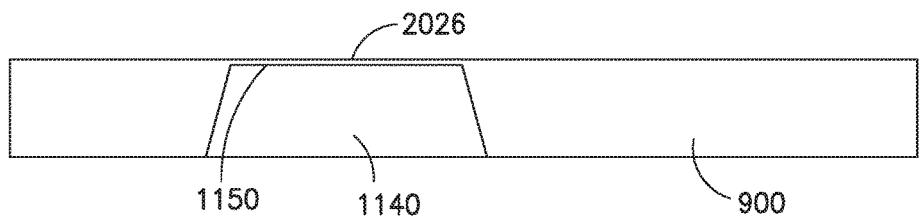
Figure 11D:
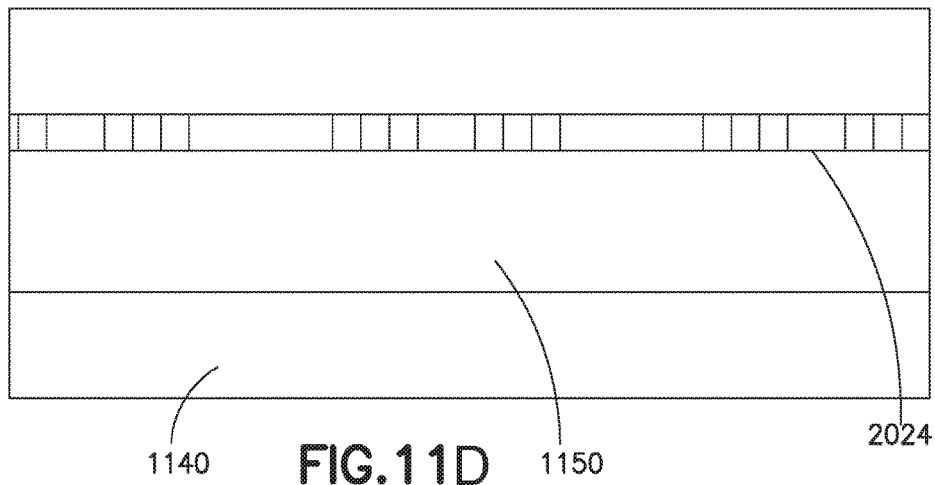

Referring to FIGS. 11A-11D, the substrate material 1100 is selected to have low thermal conductivity (<2.0 W/m-K) in order to minimize thermal losses into the substrate and cross conduction from the heating element 2024 to the sensors. The substrate material 1100 has consistent flatness, the ability to tolerate temperatures required for the deposition process, and the ability to tolerate pressures up to 1 mega-pascal. Such high pressures are caused by back pressure that is created by the use of a pen needle in which the cannula cross section is smaller than the cross section of the flow channel 1026 provided in the semi-disposable. Pen needle users often prefer small cross-section cannulas to decrease pain and discomfort during injections. Borosilicate glass is one exemplary material that may be used for the substrate 1100, but other thermally insulating materials could also be used. The preferred substrate 1100 is a single thickness, such as 0.35 mm or 0.5 mm. Alternately, a thin (such as, less than two microns) sensing membrane 1150 formed by back-etching the substrate 1100 may be manufactured. However, this sensing membrane's require structural features or other accommodations to deal with the pressure present during a dosing, or to mitigate or lessen the pressure applied to the sensing membrane during a dosing event. The thin sensing membrane 1150 design allows for the use of materials with a high thermal conductivity, such as over 2.0 W/m-k. The thin designs are more thermally efficient and have higher signal to noise ratios, but are more complex to fabricate and are more sensitive to operating pressure. Another design illustrated in FIG. 11B has etched slots 1130 serving as conductive breaks on both sides of the heater 2024 and sensor 2026 elements. This design has the same pros and cons as the back etched chip. Back-etching below the region on the chip with the heating 2024 and sensing 2026 elements should generally be avoided as it lowers mechanical integrity, leading to substrate deformation when exposed to pressure. This substrate deformation affects the heater 2024 to sensor 2026 element spacing, as well as flow velocity profile observed by the sensor elements 2026, affecting sensor accuracy and repeatability based on the observed pressure. To further reduce the effect of thermal conductivity, these two alternatives: back-etched area 1140 and conductive breaks 1130 can be combined as shown in FIGS. 11A-11D, which illustrate respectively, a top view of a sensing chip (FIG. 11A), a magnified top view of a sensing chip (FIG. 11B), a section view of a sensing chip (FIG. 11C), and a magnified section view of a sensing chip (FIG. 11D).

Exemplary embodiments of the invention form the sensor onto a glass substrate. The glass substrate has low thermal conductivity and structural rigidity to prevent deformation of the sensor during a dosing event. Forming the sensor surface on a glass substrate is preferred in the liquid medicament flow application, since preferably one sensor surface is exposed to the medicament within a flow channel, and overcomes the limitations described above in connection with thin membrane or bridge structures used on gaseous applications where pressures imparted onto the sensor are not a concern.

An exemplary microfabrication process of a hybrid TTOF sensor will now be described. The glass wafer substrate is first cleaned and conditioned to remove all surface impurities. This can be done with either solvents or via chemical etching.

A metallic adhesion layer, typically Cr or Ti, is then deposited onto the substrate to promote adhesion between the glass and the heating and sensing layers. The metallization layer preferably consists of material with a thermal expansion coefficient greater than that of the glass substrate (such as 4.0 m/(m-K)) and less than that of the gold electrical traces (such as 14 m/(m-K)). Preferable materials include chromium and titanium, but other materials could also be used. A multi-layer structure may be used to improve robustness of the bond between the heating and sensing elements and the glass substrate and minimize the potential for any delamination of the deposited layers during use.

Figure 16A:
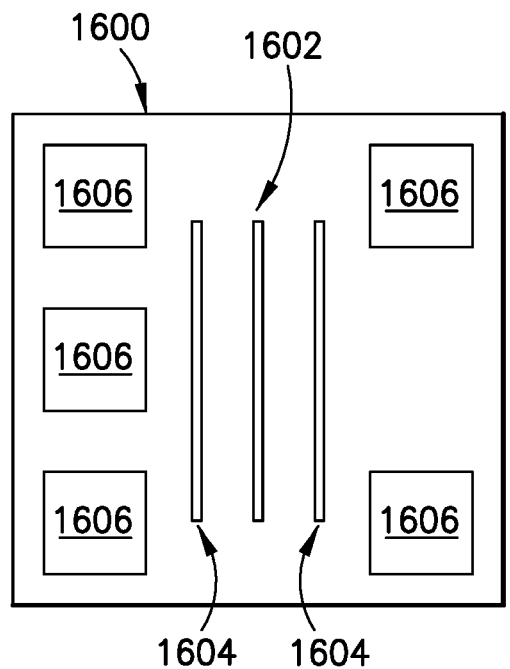
FIGS. 16A-16D illustrate a sensor chip with via features according to an exemplary embodiment of the invention.
Figure 16B:
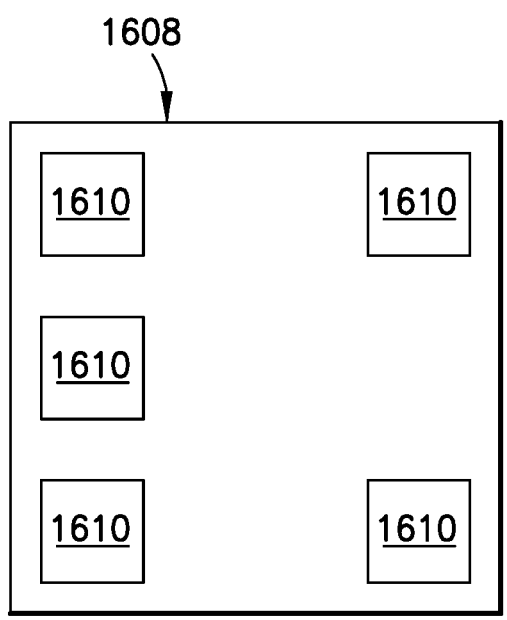
Figure 16C:
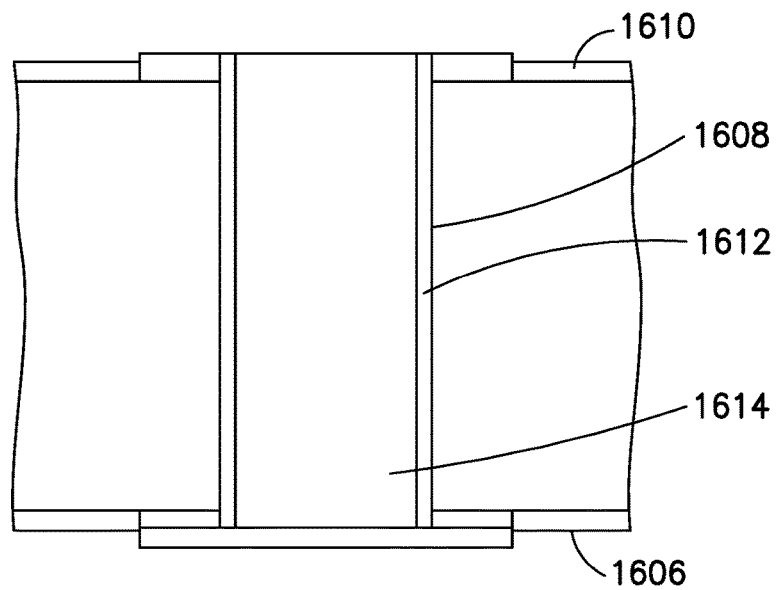
Figure 16D:
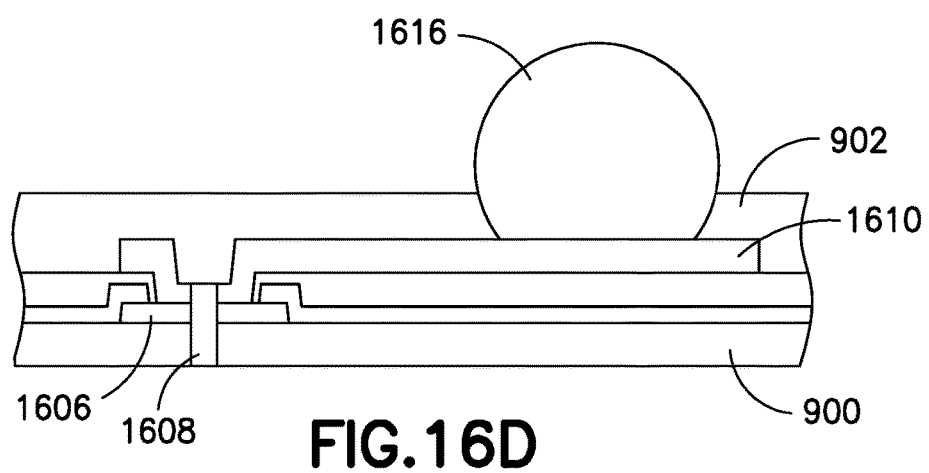

Micro-scale platinum heating and sensing elements are then deposited on the metallization layer. Platinum is preferably used due to its relatively high and linear temperature coefficient of resistivity (TCR), as well as being inert and corrosion resistant, although it should be appreciated that other suitable materials with similar properties, such as polysilicon, could be substituted. As illustrated in FIGS. 16A-16D, the element structure consists of a central heating element 1602 with paired sensing elements 1604 precisely positioned equidistant from the heating element 1602 in upstream and downstream directions. In one embodiment, the heating and sensing elements are electrically connected to electrical pads 1606 on the same surface of the chip, and vias provide electrical connectivity to the opposite side 1608 of the substrate and corresponding electrical pads 1610 on the opposite side 1608. FIG. 16C illustrates a cross section of a via area of the device, showing the solder pad 1610, electrical pad 1606, and via 1608. Also illustrated are the conductive coating 1612 and non-conductive filler 1614. FIG. 16D is a cross section view illustrating a solder ball 1616 in addition to the substrate 902, solder pad 1610, via 1608 and electrical pad 1606. The masking and deposition process allows for precise control of the thickness, width, and length of the heating 1602 and sensing 1604 elements so that their electrical resistances are matched to within 1 ohm. The low thermal mass of the elements allows for them to be heated and cooled at a high frequency. Both of these properties are important for sensor response and accuracy, and also advantageously limit the amount of heat generated, which protects the integrity of insulin flowing through the device.

Nominal resistances of between 100 and 1500 ohms may be used for a sensor according to an exemplary embodiment of the invention with preferred values being between 450 and 650 ohms based on the current electronics design for the durable portion 106.

The heater to sensor element spacing relates to the required flowrates, the thermal and fluid properties of the insulin, and electrical drive considerations. For a given flow channel cross section, the closer the elements are spaced together, the stronger the signal to noise ratio and the better the accuracy for low flow rate measurements. For a given flow rate, as the heater to sensor spacing is increased, the signal to noise ratio is reduced as more heat diffuses into the bulk of the fluid and less is carried to the sensing element. Larger spacing increases the measurable phase shift measurement range as there is a larger time of flight for the signal to reach the sensing element. Heater to sensor spacing of between 25 and 700 microns can be used, with spacing in the range of 130 to 400 microns being preferred.

Figure 17A:
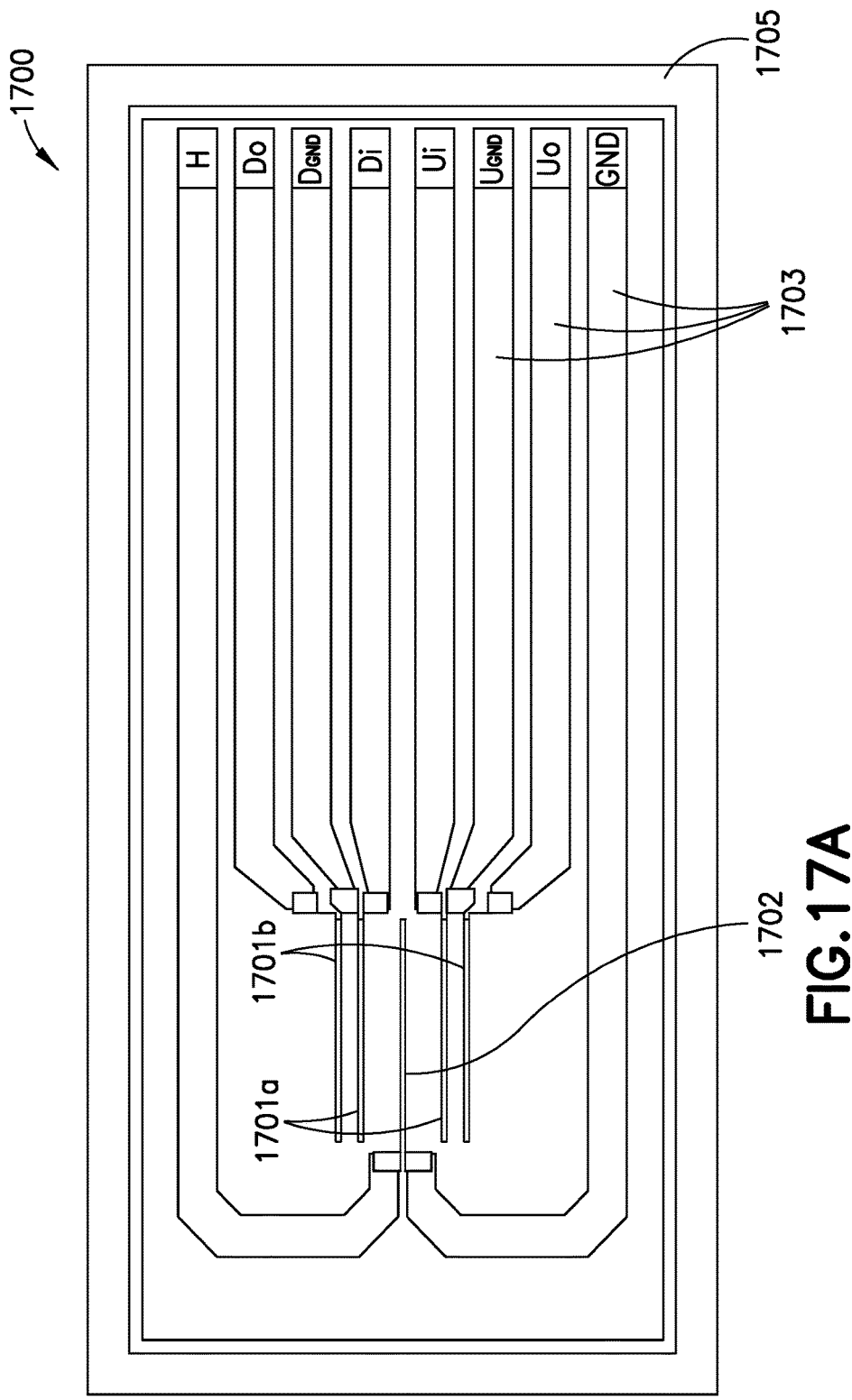
FIGS. 17A-17B illustrates a flow sensor having pairs of sensing elements according to another exemplary embodiment of the present invention.
Figure 17B:
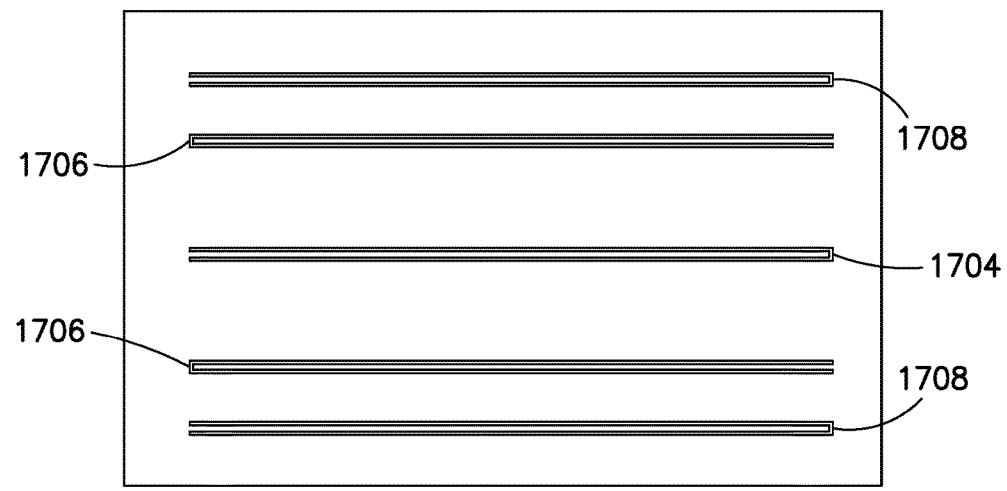

Referring to FIGS. 17A and 17B, another embodiment of the invention utilizes a sensor chip 1700 that includes two pairs of sensor elements 1701a, 1701b, with one pair 1701a being equidistant from a heating element 1702 at a first distance upstream and downstream of the heating element 1702, and a second pair 1701b being equidistant from the heating element 1702 at a second, larger distance upstream and downstream of the heating element 1702. A series of gold traces 1703 are deposited in order to connect the microstructures of the heating 1702 and sensing elements 1701a, 1701b to larger electrical contact pads used for providing wire bond connections to the mating PCBA.

The chip surface is coated with a passivation layer. The passivation layer isolates the heater and sensors from the insulin and electrically insulates the surface while minimizing thermal resistance. The layer is so thin that insulation materials such as silicon dioxide do not impart significant thermal resistance. The passivation layer can consist of multiple layers of one or more materials. Multiple thin passivation layers are preferable to a single thicker layer as a thick layer will have higher internal stresses. The use of multiple thinner layers reduces total stress, leading to a more stable passivation layer, by way of, for example, balancing tensile stress in the first layer with compressive stress in the next layer. Preferably, the passivation layer consists of a first layer of silicon dioxide and a second layer of silicon nitride. Making the overall passivation layer thicker minimizes the chance of having pin holes. The passivation layer also provides a chemically resistant and inert insulin contact surface while still maintaining high thermal conductivity. The overall thickness of the passivation layer is between 3000 and 7000 Angstrom.

A border 1705 is etched on the perimeter of each chip in order to prevent damage to the passivation surface during the cutting process to singulate each sensor on the wafer. The chip is mounted with adhesive to a printed circuit board 1202. Wire bonds are used to connect the electrical traces on the chip to the traces on the circuit board. The wire junctions are encapsulated with a protective layer of epoxy 1004 (See FIG. 10).

After assembly the sensor chips are run through a burn in process of up to 72 hours with a nominal electrical current and thermal cycling in order to stabilize their output and eliminate long term drift. The burn in process preferably also includes the flow manifold to equilibrate the full sensor.

Figure 12:
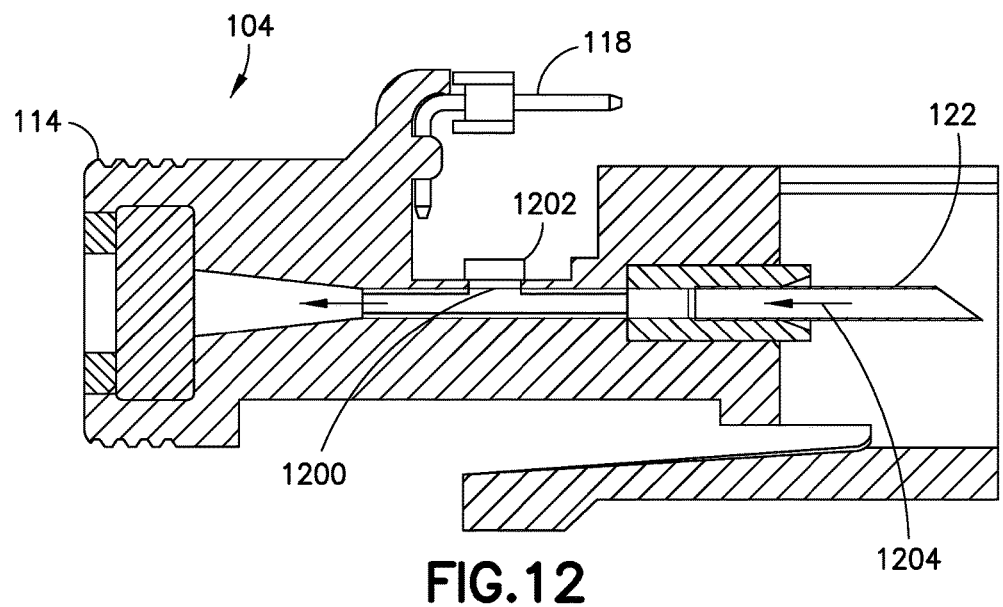
FIG. 12 illustrates a cross section of a sensor chip and flow manifold according to an exemplary embodiment of the invention.

FIG. 12 shows the sensor chip 1200 mounted onto a PCB 1202 with an exposed sensor surface within a flow manifold 1204. The chip may be mounted and sealed to the manifold 1204 by any suitable means including UV cured adhesive, molded elastomeric seals in a gland or an over-molded elastomeric seal. One end of the manifold 1204 contains a piercing cannula 122 and attaches to the ISO standard hub of an insulin pen. Attaching the manifold 1204 to the pen 102 punctures the rubber septum on the insulin cartridge and establishes an insulin flow path over the sensor 1200. The opposite end of the manifold 1204 contains threads and an elastomeric septum that create an ISO compliant connection for insulin pen needles. The manifold 1204 is formed to have minimum residual (un-recoverable) internal volume, ideally less than 30 microliters, and minimum added length, ideally less than 25 mm. The manifold 1204 includes a flow channel 1206 designed with a cross sectional area and smooth transitions to ensure that laminar flow is maintained at all times over the sensor 1200 face. The sensor 1200 face is positively positioned with respect to the channel wall so that it is always in the shear zone of the insulin flow. Sensor face positioning should be 0 mm to 0.1 mm proud with respect to the manifold wall, with 0.05 mm preferred. The flow channel 1206 through the manifold 1204 is preferably formed in a substantially straight line from inlet cannula 122 to sensor surface 1200 and on to the pen needle end to promote laminar flow of insulin through the flow channel 1206.

The manifold 1204 preferably has alignment features that ensure proper orientation and positioning of the semi-disposable portion 104 relative to the durable portion 106 during insertion and set up. A retention feature such as a snap flexure 1208 secures the semi-disposable portion 104 to the durable portion 106 and the insulin pen 102 during use and allows the user to release and remove the semi-disposable when the pen 102 is empty. An electrical connector 118 on the manifold 1204 is preferably oriented in the same direction as the inlet cannula 122 and establishes electrical contact with the durable portion 106 at the same time the flow path is being established when inserting the semi disposable portion 104 into the durable portion 106. The electrical connector 118 shown in FIG. 12 has conductive pins, but other features such as conductive pads, flexible cables, conductive flexures, or pins could also be used.

For a given sensing chip with an established heater to sensor spacing, the measurable flow range can be adjusted by changing the flow channel cross section. For a given flow rate, a larger cross section will reduce the apparent velocity observed by the chip, allowing the chip to measure higher flow rates before the sensor signal saturates. The larger cross section will have an inherent trade off of reduced accuracy for low flow rates. A smaller cross section can be paired with a larger element spacing to measure an equivalent flow range with reduced internal volume in the flow path.

The semi-disposable 104, and more specifically the elements comprising the flow channel 1206 are preferably designed with materials that are compatible and non-binding with insulin for the full life of the pen injector, that is, up to at least 28 days. Such materials include ABS plastic and 304 series stainless steel, among others. If liquid silicone rubber is used for the seal between the PCB and the manifold, and since elastomers have tendency to adsorb the preservative from the insulin, the exposed surface of the rubber seal is minimized. Medical grade light cured adhesives are used to bond manifold components. These preferably include flash cured cyanoacrylates or light cured acrylics.

The insulin flow channel 1204 is designed with gradual flow transitions in order to avoid any zones of high shear, which could potentially damage the insulin protein molecules. The manifold threaded hub 114 is preferably designed to accept ISO standard insulin pen needles.

Figure 13:
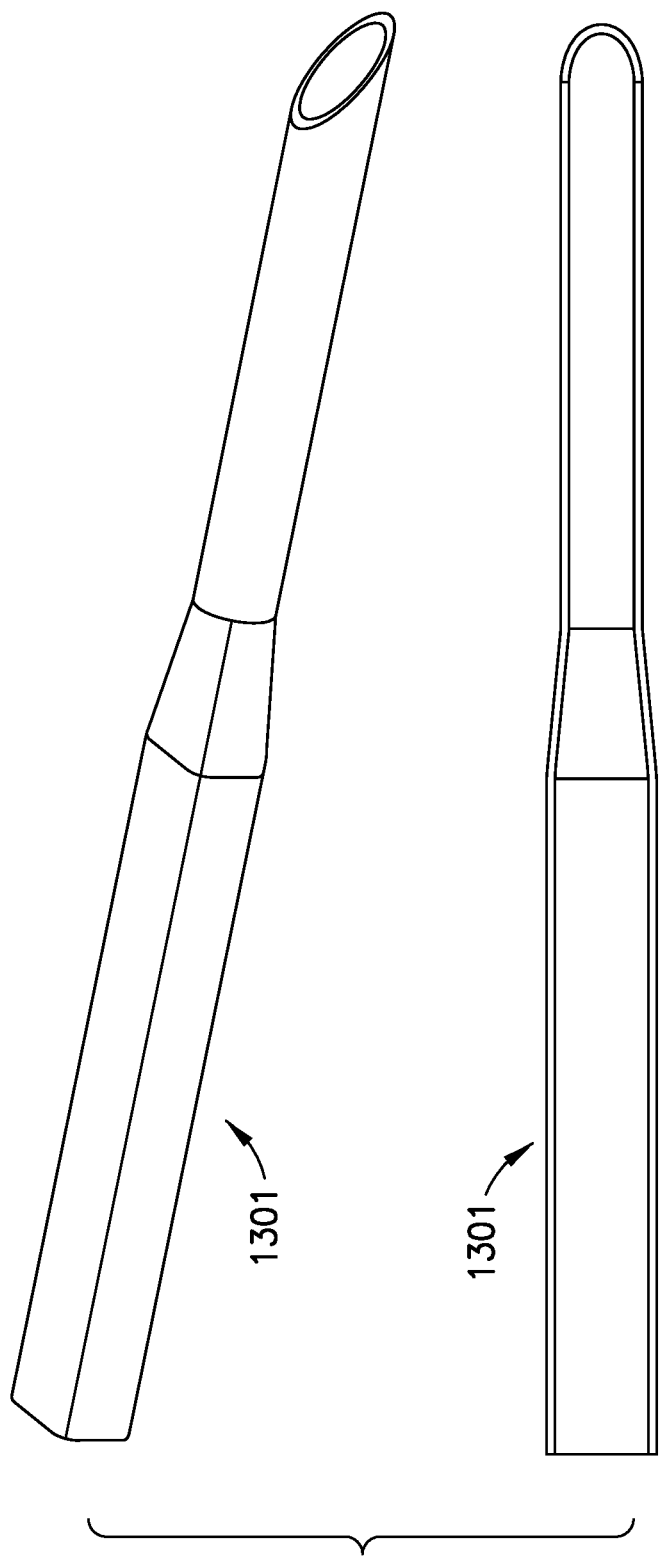
FIG. 13 illustrates a micro-fabricated flow path utilized in an exemplary embodiment of the invention.

The insulin flow channel 1204 illustrated in FIG. 12 is an injection molded thermoplastic component. Alternately, as shown in FIG. 13, the flow channel 1204 of the semi-disposable 104 could be replaced with metal, plastic, ceramic, or composite tubing 1301 that has been micro-fabricated to provide the smooth flow transitions described above. The micro-fabricated flow path allows for tighter manufacturing tolerances, which is beneficial to accuracy. The metallic flow channel 1301 is insert-molded and incorporated into the semi-disposable 104.

In another embodiment, the pen needle (PN) is manufactured as two separate components, that is, the PN hub or base, and a needle sub-assembly. The flow channel would be incorporated into the PN hub and the PN hub would attach to the standard ISO engagement provided on any insulin injection pen, remaining attached to the pen for the entire use life of the pen. The PN hub would also include an over-molded MEMS chip in which the thermistor traces are suspended or exposed within the flow channel, as described above. The smallest form factor of the MEMS chip is approximately 1.4 mm square, and to enable electrical connection between this chip and the durable element, i.e. to provide electrical contact pads sufficient in size, the MEMS chip is attached to a mini-PCBA. The needle sub-assembly is comprised of the cannula or sharp with an over-molded sleeve (as described in numerous BD patent applications, e.g. Revolver). Multiple needle sub-assemblies can be included in the pen cap or a separate needle exchanger that is used in combination with the system. Those of ordinary skill in the art will appreciate that embodiments of the present invention may be used in combination with multiple needle magazines or pen needle exchangers, such as those described, for example, in U.S. Provisional Application Nos. 62/328,967, 62/328,670, 62/328,649, 62/328,682, 62/328,702, 62/328,680, 62/328,646, 62/328,655, 62/328,654, 62/328,714, 62/328,666, 62/328,660, and 62/328,676, filed Apr. 28, 2016, the entire contents of which are incorporated herein by reference.

Another alternative is to utilize the MEMS fabrication process to produce a highly accurate flow channel. This alternative could be comprised of either two or three MEMS elements, which could be composed of either Si or Borosilicate glass or a combination of both. Si is preferred since higher accuracy can be achieved when etching vias and back etched surfaces, but glass provides superior mechanical and thermal properties as a substrate for the thermistor traces.

Figure 14A:
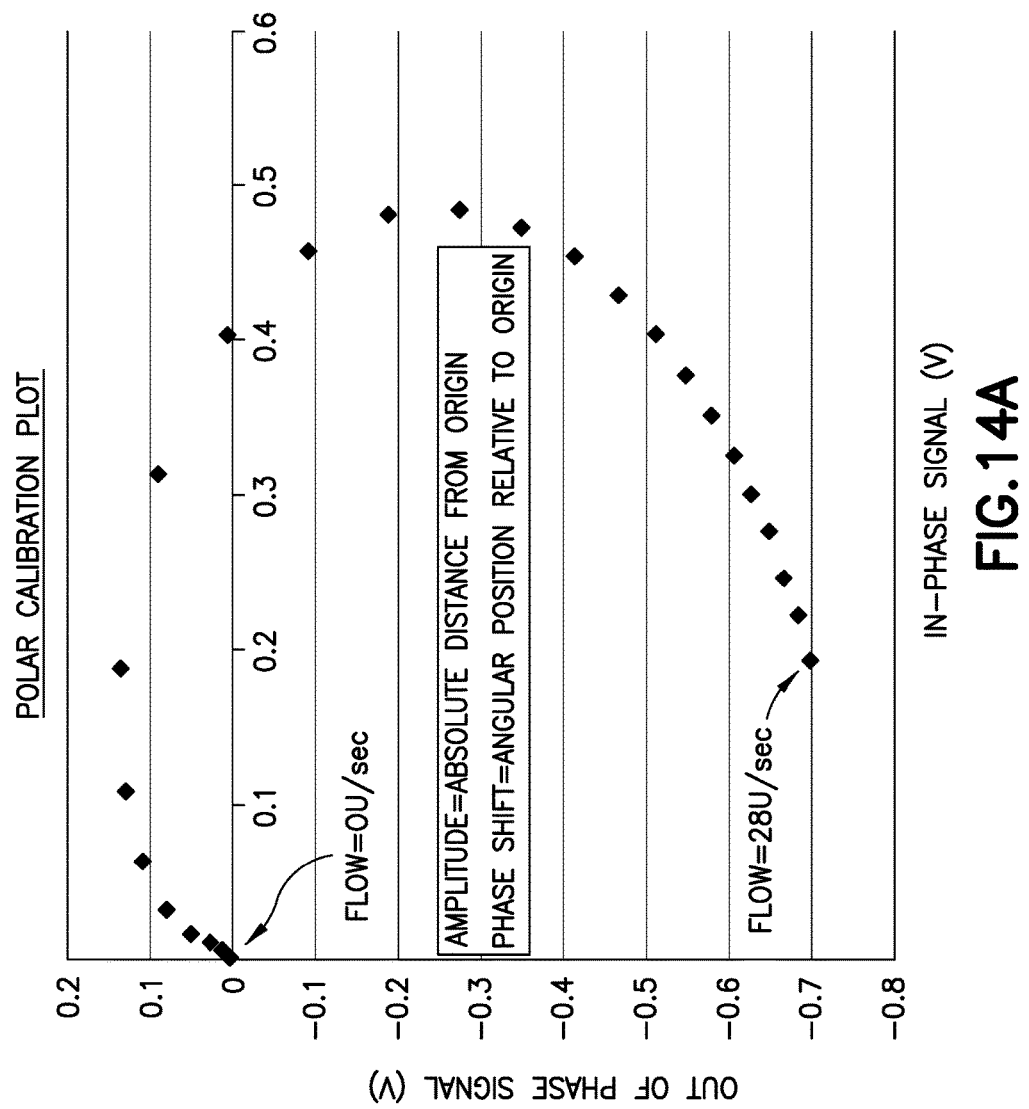
Figure 14B:
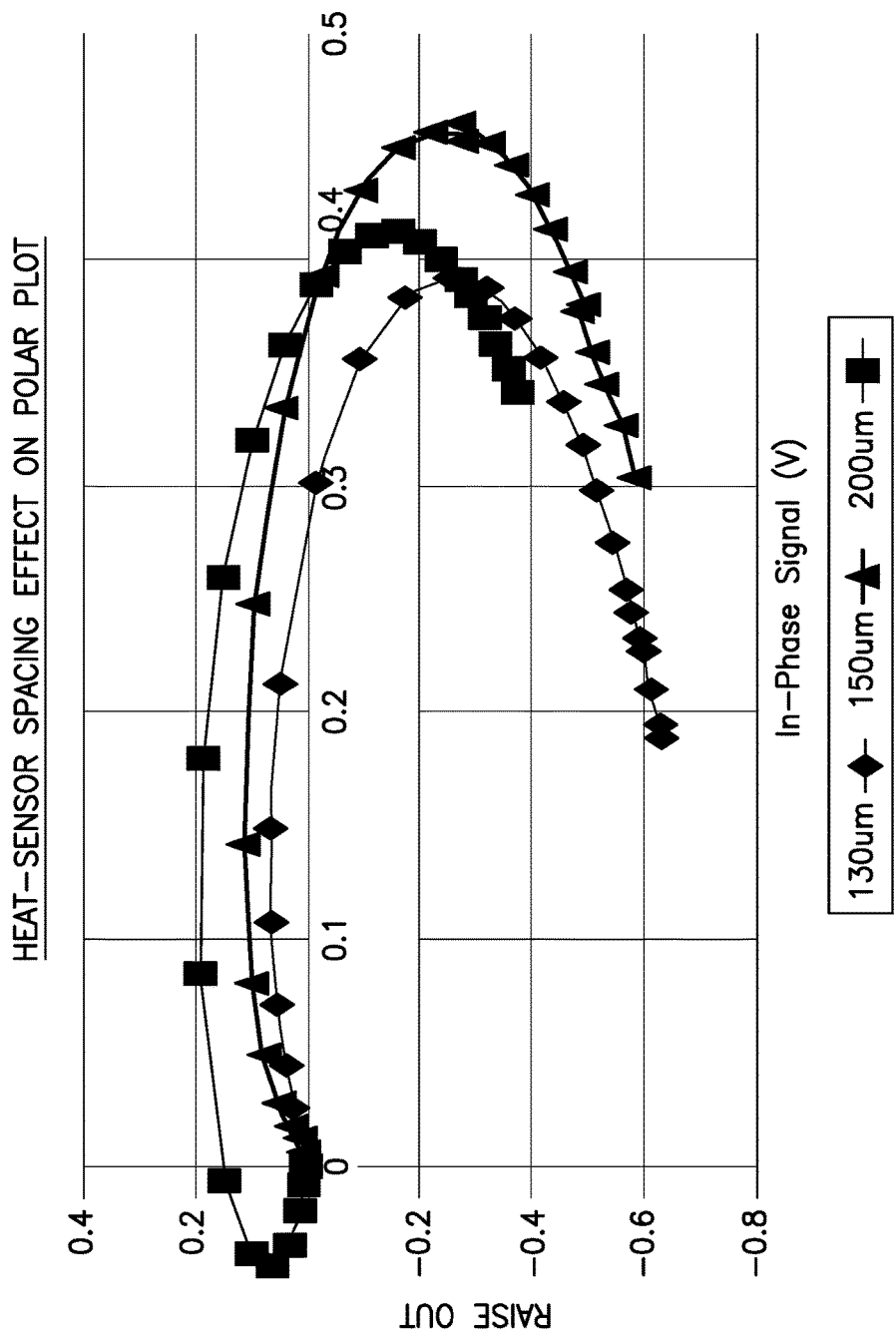

FIG. 14A shows a polar calibration plot of phase and amplitude components of the sensor signal. The amplitude is represented by the radial dimension of the plot and the phase is represented by the angular dimension. Both phasor components are used for calibration. At low flow rates, the amplitude is used to determine flow. At higher flow rates the phase shift is used to determine flow.

For calibration, in one exemplary embodiment the dose sensing system uses individual calibrations for each semi-disposable portion 104 that is manufactured. The calibrations are accessed via a look up table stored in the durable portion 106 firmware, or alternately may be stored in the cell phone 108 application, or in a secure cloud storage associated with each patient. In another exemplary embodiment, tight tolerances are required for manufacture of the sensor and manifold features, and a universal calibration is pre-programmed for all or a particular lot of manufactured semi-disposable portions 104.

In another exemplary embodiment, each manufactured semi-disposable portion 104 is individually calibrated. The calibration information is stored in a memory chip on the disposable portion 104, and the durable portion 106 automatically reads the calibration information during set up.

In another embodiment, flow rates are measured for a particular lot of manufactured semi-disposable portions 104, and lot specific calibration information is added to a memory chip or a bar code label on the disposable portion 104. The durable portion 106 reads the calibration information during set up.

In another embodiment of the invention, flow rates are measured for a particular lot sample of semi-disposable portions 104, and a code related to calibration data is included on or in the semi-disposable portion 104 packaging. The user enters the code in the cell phone 108 application, and the application in turn transfers the calibration data to the durable portion 106.

In another embodiment of the present invention, the user verifies the first dose or first few doses delivered from the pen after the initial setup. The system then scales the stored calibration data to match the intended dose. If the intended dose and the measured dose have a mismatch greater than a permissible error, then the cell phone 108 application initiates troubleshooting steps. For example, the user can enter the selected dose volume in the smart phone application. The actual volume measured by the flow sensor can then be compared to the intended dose, and corrective actions may be taken, such as adjusting the algorithm with an offset value for a specific range of the flow rate.

Figure 15A:
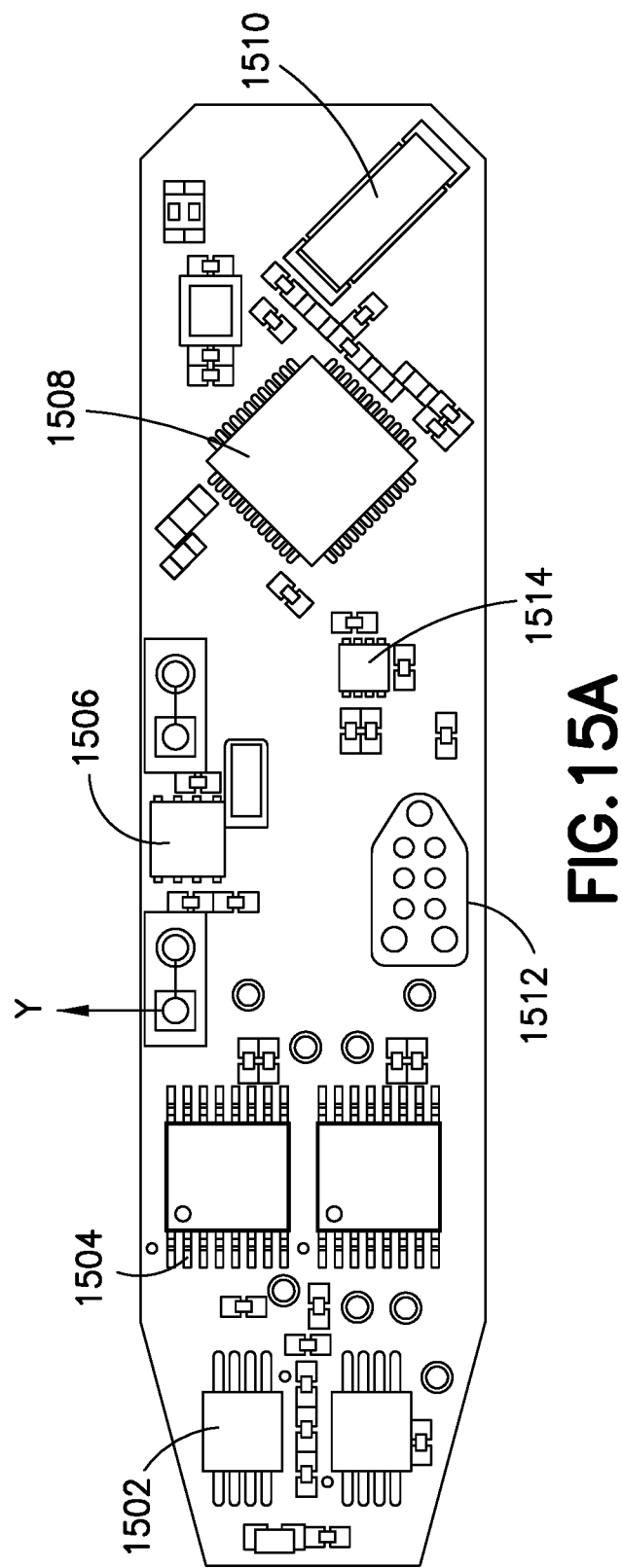
FIG. 15A-15B illustrates a circuit board of a sensor device according to an exemplary embodiment of the invention.
Figure 15B:
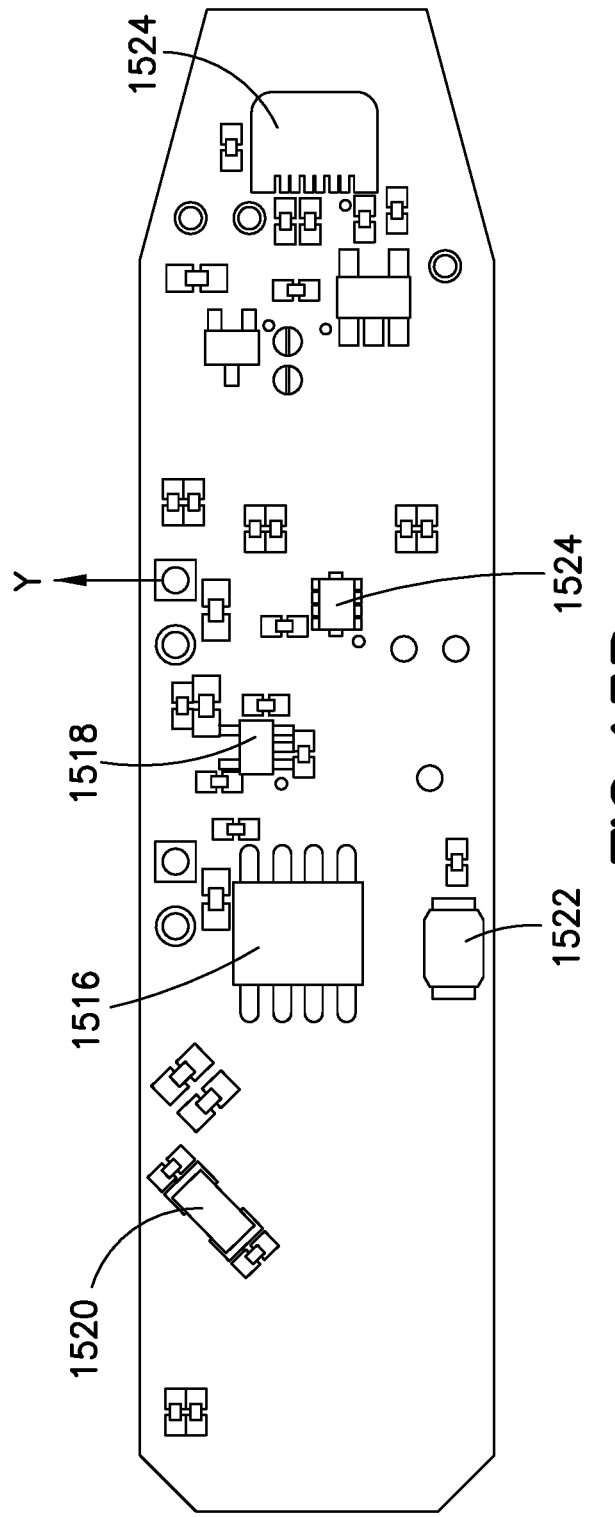

In yet another embodiment of the present invention, a set of pre-stored calibration curves are stored in a memory of the durable portion 106. The priming dose is used to select the best matching calibration curve among the set of stored calibration curves. HERE FIGS. 15A and 15B show the electronic control board and the major components of the control circuit. As illustrated in FIG. 15A, top of an exemplary board includes a microcontroller 1508, Bluetooth antenna 1510, demodulator 1504, instrumentation amplifier 1502 and battery charge control/regulator chip 1506. FIG. 15B illustrates an exemplary board bottom which includes a cap switch 1522 that indicates removal or attachment of the pen cap, accelerometer 1514, analog to digital converter 1524, load switch 1518, flash memory 1516, real time clock 1520 and sensor connector 1524.

An exemplary system will now be described. The system is preferably powered using a 3.7 volt lithium polymer re-chargeable battery. The power source is regulated to 3.3 volts using a low dropout (LDO) linear regulator 1506. An interlock switch 1522 tied in to the device cap 146, along with an additional motion sensor 1514, is used to automatically start and stop the heater to conserve power. If the cap is removed and the unit is moving, the heater drive circuit is energized and the system is ready to record doses. If the system is quiescent for more than 30 seconds and/or the cap is replaced, the heater is automatically turned off to conserve power. An exemplary method of operating an embodiment of the present invention, including utilizing cap and motion sensors to conserve energy, will now be described in connection with the state transition diagram of FIG. 23. At state 2300, the device is initialized. During initialization, various features in the processor and peripherals are setup. During initialization, preferably a red and green LED are lit until setup is complete. Initialized features include, for example, a GPIO and associated interrupts, timers, SPI pins, flash memory, a BLE stack, demodulators, an external ADC, an accelerometer, a task scheduler, various BLE parameters, an internal ADC, a master clock, battery voltage reading, a real-time clock, BLE advertising, and assessment of pen cap state. Once initialization is complete, if the pen cap is on, the control method moves to state 2301, idle, cap on. In state 2301, the battery voltage is sampled every 30 seconds at state 2302, and then returns to state 2301 when sampling is complete. During the idle, cap on state 2301, a timer initiates Bluetooth advertising mode 2303 every five (5) seconds. The Bluetooth advertising mode lasts four (4) seconds, and permits other devices to connect to the durable portion. After four (4) seconds, the control mode returns to state 2301. If a device connects during advertising mode 2303, the control method moves to state 2304, during which the battery level is updated, and then the control method moves to state 2305, the Bluetooth connected, idle state. While connected, the connected device may initiate several procedures. The connected device may initiate a time update, during which the device clock is updated in state 2306. After the clock is updated, the control method returns to state 2305. The connected device can initiate a calibration table sync, during which the control method first recalls the calibration table during state 2307, then when the calibration table is recalled, data is transmitted to the connected device during state 2308. After data transfer is complete the control method returns to the Bluetooth connected, idle state 2305. The connected device can also initiate a data sync, during which the control method moves to state 2309, during which event data is recalled from memory. The recalled data is then sent to the connected device in state 2308, and once the data transfer is complete, the control method returns to state 2305.

After initiation 2300, if the cap is detected to be off, then the control method moves to state 2310, during which the analog circuit is turned on and data is collected and buffered. Also, if the device is in any of cap-on states 2301-2308, and the device cap is removed, the control method moves to state 2310 if the motion detector has detected movement in the last 30 seconds, or to idle, cap off state 2311 if motion has not been detected in the last 30 seconds. While in state 2310, if the device is stationary for 30 seconds (no movement detected), then the control method moves to idle, cap off state 2311, and moves back to state 2310 if movement is subsequently detected. If an event is detected during state 2310, then the control method moves to awaiting event end state 2312. Once the event end is detected the control method moves to storing detected event to flash state 2313. Once data storage is complete, if movement was detect in the last 30 seconds, the control method moves to state 2310, if not the control method moves to state 2311. At any time during the cap off states 2310-2313, if the cap is placed back on the device, then the control method moves to idle, cap on state 2301.

Precise control of the heater drive signal is necessary for repeatable and stable sensor operation. According to an exemplary embodiment of the invention, a constant frequency signal is used to drive the heating element. A square or sinusoidal signal in the range of 20 to 200 Hz is used for the heater, with a square wave in the range of 50 to 100 Hz being preferred. The driving frequency is limited by the thermal properties of the heating element. The driving frequency affects amplitude and phase resolution of the heater signal and subsequent sensor response. Driving the heater at too high of a frequency results in the loss of amplitude due to thermal lags. Driving the heater at too low of a frequency results in the loss of transient response time. The heater driving frequency should be different from the expected environmental frequencies to reduce signal noise.

The heater is driven in a range of between 5 mW and 30 mW at a constant voltage with a current limiting resistor. To refine the signal to noise ratio for a given chip, the heating drive power can be adjusted by changing the value of the current limiting resistor. This will cause the heater to output more or less heat into the fluid, and subsequently cause more or less heat to be carried to the sensor element during flow. A lower heat driving frequency in combination with a higher heater power input can be used to increase the heater signal amplitude and signal to noise ratio.

The heater is preferably a thermistor whose resistance and resulting current change with temperature, and so a constant voltage drive can have some thermally induced variability during operation. An alternate heater drive scheme using constant current with a feedback mechanism such as voltage feedback on a current sense resistor could be used for more precise control. A heater drive with constant power operation provided by feedback on both current and voltage could further improve the level of heater control.

Signals from the upstream and downstream sensors are read by the electronics. The signals are time varying waveforms with a diminished amplitude and shifted phase relative to the heater drive signal. The signals are on the microvolt scale and are susceptible to electrical, thermal, and mechanical induced noise.

The sensor operates using the principle of IQ demodulation, applied in the circuit with the use of two synchronous demodulators and analog filter chips. The theory of IQ demodulation provides in-phase and out-of-phase (quadrature) DC signals in response to a carrier frequency emitted from one thermistor element to another thermistor element located some distance away. The carrier frequency is compared with the return signal from the receiver, put through a convolution stage that provides a DC signal output, that is, an in-phase component of a resultant vector. The carrier frequency is shifted 90 degrees and is compared with the return signal, the out-of-phase DC signal, that is, the quadrature component of the resultant vector. These two output signals currently require two discrete demodulator chips in the circuit, one has register values set for in-phase comparison and the second is set for 90 degrees out of phase. The two resultant signals are low pass filtered and measured by an analog to digital converter chip. These circuit stages could also be fulfilled by using an application specific integrated circuit (ASIC) that contains all required circuitry and register/gain/clock settings in a single small package.

The return signal of the sensor is conditioned using an instrumentation amplifier, high pass filter and AC gain stage referenced to a mid-point voltage provided by the demodulator chip. The instrumentation amplifier uses the same reference voltage and measures the upstream and downstream sensing elements in a differential configuration. The precision reference holds a stable baseline for the resultant signal. The differential configuration of the instrumentation amplifier removes common mode noise, this allows for a stable baseline when no fluid flow is occurring as any external noise is seen as a common mode signal on both upstream and downstream sensing elements. This configuration also provides for stable output as ambient temperature changes. A gain value is set using external resistors which provides an optimal operating range for the output signal. Once flow is occurring, the upstream sensor receives an attenuated signal from the carrier frequency and the instrumentation output shows the amplified signal seen on the downstream sensor with common mode noise removed. This signal will be a time shifted version of the carrier frequency. The amplitude variation of this signal will depend on the distance from heater to sensor and diffusion of the signal into the fluid, as well as a gain factor designed into the amplifier. The gain is preferably set to avoid clipping of the output signals due to saturation at the voltage rails of the amplifier, but high enough so that the resolution of the signals will be sufficient for accurate readings.

The two resultant signals from the demodulator chips can be recombined into a vector which includes amplitude and phase components, as shown in FIG. 14A. FIG. 14A shows many points that correspond to various flow rates from 0-1000 mL/hr (0-28 U/sec). Each point has an in-phase (x) and out-of-phase (y) component. Together, they show an amplitude and phase trend on the polar plot. This can be interpreted as a 'speed gauge' and calibration to flow rate allows for accurate instantaneous measurement. Fluid velocity measurements over time allows for accurate volumetric dose calculations. The phase (that is, the time of flight) component of the resultant vector is more immune to thermal noise and allows for better resolution of 100-1000 mL/hr flow rate measurements. The amplitude or signal voltage threshold is used to determine flow or no-flow conditions. If the sensor is designed with multiple channels or a higher phase resolution, the amplitude is used to switch between various flow rate regions, where phase values provide a high precision value. For example, if the phase range were to be $0-4*\pi$ radian, amplitude measurements between 0.1V and 1V yield flows rate between 50 and 500 mL/hr. The precise flow rate in this range would correlate to $0-2*\pi$ radian phase value. However if amplitude measurements were over 1V, the flow rate range of 500-1000 mL/hr would correlate to $0-2*\pi$ radian phase values on a second channel or region of the polar plot. The above described method provides for infinite flow range or precision providing infinite periodic phase cycles and region or channel thresholds.

A system response time of less than 60 ms is desirable to accurately capture the rapidly changing signals from the sensor during dosing. In exemplary embodiments of the invention, as described herein, the term "response time" is defined as the time from the start of a flow event to the time before the sensor measures an accurate flow rate value within 95% accuracy of the true value. This response time is significantly faster than commercially available flow sensors, which typically have effective response times greater than 500 ms. The improved response time is achieved by tuning the high and low pass signal filters to achieve a slightly under-damped response to expected transient signals. Underdamping allows for the sensor signal to change more rapidly, but results in some oscillation about the true steady state flow value. Selecting a sampling rate above 100 Hz minimizes any aliasing of the output signal and enables the system to calculate an accurate running average of both the in phase and quadrature signals that represent the sensor response to fluid velocity.

The sampling rate is limited by the frequency of the driver & demodulator chips, which allow for 8 samples per period of the drive waveform, resulting in a maximum sampling rate of 440 Hz with the current drive frequency of 55 Hz.

The electrical circuit eliminates baseline signal noise in the system, which advantageously improves the sensor signal repeatability and accuracy.

A flow sensing algorithm for use with a flow sensor according to an exemplary embodiment of the invention will now be described. The algorithm advantageously utilizes both calorimetric (amplitude) as well as thermal time of flight (phase) sensing for flow rate measurements. The magnitude of the heat signal carried by flow from the heater element to the downstream sensing element is determined as the amplitude signal. The amplitude signal represents the calorimetric sensing portion of the algorithm. The phase shift as measured by the delay between the heater signal and the received signal by the sensor is the thermal time of flight portion of the algorithm. The amplitude signal value is used to determine when flow is occurring. Once the amplitude signal indicates the presence of flow, the phase shift value is used to determine the flow rate.

During dose capture mode, the dose sensing algorithm continuously monitors the analog signal values output by the sensor. In this device state, data is stored in a rolling buffer, and the device is continuously analyzing the buffer for a dose start condition. A dose event is detected when the two analog signal values from the sensor elements change relative to the baseline. The signals can either diverge from each other, or the amplitude of the signals can exceed a preset threshold. A stop condition is determined when the signals converge or reduce amplitude to within a set threshold. The data recorded between the start and stop condition is transferred from the rolling buffer to system flash memory along with appropriate metadata, which can include real time clock, temperature, accelerometer, sensor identification, and other data. Alternately, data is processed in real time without transfer to a buffer.

After the dose data is transferred to flash memory, the dose sensing algorithm is used to determine the dose volume of the flow event. The algorithm utilizes both calorimetric as well as thermal time of flight sensing techniques to determine the flowrate. Calorimetric sensing uses amplitude of a heat pulse observed by thermistors placed upstream and downstream in the flowpath. Thermal time of flight is measured by the phase shift (time delay) between the heater signal and the signals measured by the sensing thermistors. A signal conditioning circuit produces in-phase and quadrature demodulator outputs I & Q. (See IQ demodulator section for mode detail on how these outputs are created). Amplitude and phase shift values are calculated for each data sample and are recorded in memory. A stored calibration is used as a lookup table to calculate flowrate for both amplitude and phase shift. The amplitude signal value is used to determine when flow is occurring. When the amplitude value is above a preset threshold, the phase shift calculated flowrate is selected as the "true" flowrate. When the amplitude value is below the threshold, the amplitude calculated flowrate is selected at the "true" value. The calorimetric sense mode of the sensor has greater accuracy at low flow rates. Time of flight sense mode has greater accuracy at high flow rates. Using both modes creates a hybrid sensing system with improved dynamic range relative to either single mode system. FIG. 5 shows flow rate data plotted versus time. The area under this curve represents the dose volume delivered. In the example hardware, a simple reimann squares method of integrating the dose volume is employed by the algorithm. Another method to calculate dose volume from flow rate data could be a curve fit function integrated with respect to time, or any other suitable integration method.

An event finder determines when a dose event occurs and subsequently records the data for the dose event. The event finder simultaneously monitors the cap switch 1522, the accelerometer, and the flow sensor to determine that a flow event is likely and to prepare the system to accept data by turning on the heater and microprocessor.

A state transition control scheme, such as the one described above in connection with FIG. 23, is built into the firmware of the embedded system. This monitors the pen cap state (on/off) and accelerometer interrupts when motion exceeds a setpoint threshold. The sensing system preferably activates when the pen cap is removed and motion has been sensed. In this mode, the heater sends a carrier frequency, powering a thermistor and pulsing heat on the sensor chip. The analog to digital converter collects resultant signal data and logs it into a buffer. The buffer preferably holds 5-15 seconds of data. The processor evaluates the data buffer during this time to see if an amplitude value is larger than a set threshold. Alternately, the trigger can be set by diverging resultant signals which corresponds to low flow conditions. When the start of flow condition is met in firmware, the time is recorded. A similar end of flow condition is recorded when signals return to baseline after flow has stopped. At this point, the buffer stops recording new data and the data from start to stop time are recorded in flash memory, along with a time stamp (real time UTC value) and other pertinent metadata. The heater is turned off when the cap is placed on the device or if no motion is sensed for a predetermined time period such as 30 seconds.

Bluetooth data transfer to a cloud connected device requires an initial pairing of the durable device. Once the durable device has been paired, encrypted data transfer will commence without user involvement when a trusted device has good signal strength (RSSI, within 100 m) and new data is ready. The cloud device requires an installed application (passively running in background mode) to communicate with the durable when within range. The Bluetooth service on the durable device runs on a limited advertising interval to conserve battery power. This allows a device to connect within reasonable time period (<10 seconds) when in range.

The software application preferably connects to the durable portion 106 via Bluetooth Low Energy (v4) protocol, or any other suitable wireless communication protocol. The application uses two standard Bluetooth profiles to provide or receive updates; the standard battery service receives the State of Charge (SoC) percentage in the form of a decimal value (0-100), the real-time clock data on the device is updated using a standard clock service which sends the device the current UTC time stored in the application. A custom Bluetooth service updates dose event data stored in the application from flash memory in the durable portion 106. The dose event data preferably includes a header that details time and date, sensor ID, error flags and other metadata, and also includes the raw sampled data from the device. Alternately, data processed within the durable portion 106 could be provided directly to the application.

The application stores dose information for the user to review and share. This data is preferably encrypted appropriately to provide privacy and otherwise comply with HIPAA requirements. The application further preferably provides the user the ability to import other pertinent data that allows for a deeper analysis of their state of health; such as data from blood glucose monitors, activity trackers, food journal applications, electronic health records and other sources. The application will show a data overview to measure trends and provide meaning from the aggregated data. The application also preferably provides a log book history of discrete doses that can be reviewed by the user or a healthcare partner. A graphing screen shows trends and data points over time. FIGS. 4A-4C illustrate exemplary screenshots of the application. FIG. 4A illustrates display of an individual dose that has been recorded, FIG. 4B illustrates display of dose history information, and FIG. 4C illustrates display of dose graphs based on recorded dose events.

The sensor embodiment described above uses a wire bond process to connect the electrical traces on the sensing chip to the (larger) electrical traces on the printed circuit board. Wire bonding is a common, cost effective process for producing electrical connections between MEMS scale circuits and printed circuit board assemblies (PCBAs), but it requires the connecting wires to be on the same side of the sensing chip as the heating and flow sensing features. In this configuration, the wire bonded sensor requires a three dimensional fluid seal with the flow manifold, which is complex. An alternate sensing chip design utilizes etched and filled vias to route the electrical connections on the sensor chip to the back surface. The fluid seal can then be made to the planar face of the chip containing the heater and sensor traces and the electrical connections to the circuit board can be made to the planar back surface of the chip. The via based design can be used to improve the robustness of the fluid seal and the speed of assembly, reducing overall cost. One potential layout of the via based sensing chip is shown in FIGS. 16A and 16B. FIG. 16A illustrates a fluid facing surface 1600 of the sensor ship. The heater element 1602, and two sensing elements 1604 are provided, along with several vias 1606 to provide electrical connections to the reverse side of the sensor. FIG. 16B illustrates the reverse surface 1608 with electrical connections 1610 for easier connection to the remainder of the device.

A silicon and glass via chip design variant is preferable to the glass wire bond chip design. The glass and silicon wafers are bonded together before or after channels are created. The via channels 1606 in the glass substrate can be made using a drill or laser. Conductive material is deposited into the via 1606 to allow for signals to travel through the chip. If conductive material is deposited around the diameter of the via, then the remainder of the via is preferably filled with non-conductive material. This allows for traces connected to the sensing elements 1604 on the top side 1600 to be routed to solder pads 1610 on the bottom side 1608 of the chip die. The pads 1610 on the bottom of the chip resemble a ball grid array (BGA) design. This allows for a standard pick and place assembly process that achieves a more reliable sensor component to be built into the flow manifold.

In an alternate embodiment of the invention, a different number of sensing elements can be used to increase the measurable flow range and accuracy of the sensor. For a given heater to sensor spacing, the sensor element can measure a certain velocity range. Having additional sensing elements at another spacing allows for a different velocity range to be measured using the additional elements, resulting in an overall wider measurable velocity range or greater accuracy over a narrower velocity range. For a chip with a single heating element and a plurality of sensing elements, each having a paired upstream differential element, in a given flow channel cross section, one given element spacing, such as 130 µm, can be used to measure one flow range, such as 20 to 300 mL/hr, while a pair of elements with a different spacing, such as 200 um, can be used to measure a different flow range, such as 200 to 1600 mL/hr. FIG. 17A illustrates an exemplary sensor chip design having multiple sensor pairs. FIG. 17A illustrates the fluid facing chip surface 1700, and the sensor zone 1702. FIG. 7B illustrates the sensor zone 1702 in more detail. A single heater element 1704 is provided, along with a first sensor element pair 1706 at a first offset distance from the heater element 1704, and a second sensor element pair 1708 at a second offset distance from the heater element 1704 that is greater than the first offset distance.

Figure 18:
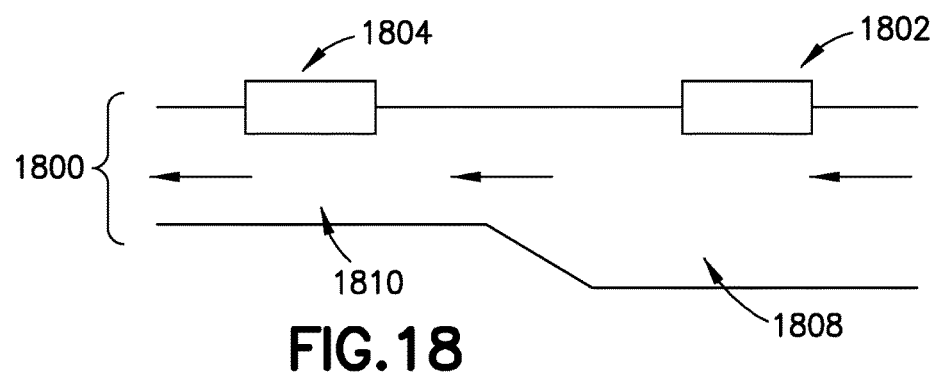
FIG. 18 illustrates a device having tandem sensor chips according to another exemplary embodiment of the present invention.

In another exemplary embodiment of the invention, multiple sensor chips are used in tandem to increase the dynamic range of the sensor. FIG. 18 illustrates an alternate flow channel 1800 having a first sensor 1802 and a second sensor 1804 downstream from the first sensor 1802. The flow channel 1806 is provided with two different cross section zones corresponding to the two sensor chips. The first sensor 1802 can be placed in a relatively larger flow cross section 1808 within the flow channel 1806. This sensor will have better resolution at higher flow rates due to relatively lower flow rates. The second sensor 1804 is placed downstream of the first sensor 1802 in an area of the flow channel 1806 having a smaller cross section 1810. The second sensor 1804 will have better resolution at lower flow rates due to relatively higher flow rates. Of course, one of ordinary skill in the art will readily appreciate that more than two sensors can be used to further improve dynamic range if necessary. The dose sensing algorithm determines the appropriate sensor pair to power and read signals from based on measured flow conditions and trends.

The multiple sensing elements may all be powered and in use, allowing post processing to determine the flow rate. Alternately, a multiplexer is used to reduce the complexity of the electronics required. In this embodiment, the heating element is powered, emitting the heat signal. Based on optimal flow rate ranges for each of the sensing element pairs, the appropriate sensing element pair can be used based on the calculated flow rate. For example during low flow condition the device uses the 130 um spaced elements and does not measure the signal from the other spaced elements, while during high flow condition the 200 um spaced elements are measured while the other elements are not measured.

Proper procedure for injections requires the user to install a new pen needle for every injection. To ensure conformance to this procedure, exemplary embodiments of the invention include a switch or proximity sensor, or the like, to either the semi-durable portion 104 or the durable portion 106 to detect the presence and removal of the pen needle.

A dose sensor according to an embodiment of the invention can advantageously detect whether or not the user primes the pen needle prior to injecting. Priming ensures that the needle is not obstructed, and that the user receives the intended dose. The flow sensor as described herein is advantageously able to sense small transient doses of 1 or 2 units which can occur in less than 0.5 seconds. The detected priming dose can be recorded separately to more accurately determine the dose delivered and the amount of insulin remaining in the reservoir of the insulin pen.

A dose sensor according to an embodiment of the invention can advantageously detect the hold time after delivery and provide feedback that the entire dose has been delivered. The device can additionally indicate to the user via visual or auditory feedback when the entire dose has been delivered.

A dose sensor according to an exemplary embodiment of the invention can advantageously sense a partial dose delivery event. The accelerometer 1514 in the durable portion 106 can track the motion of the insulin pen 102 during the injection. If the pen 102 moves before the dose delivery is complete, the device can sense this and provide warnings and feedback to the user. The partial dose delivered and amount of dose lost can be constructed from the flow and accelerometer readings and relayed to the user.

A dose sensor according to an exemplary embodiment can advantageously sense different medications dispensed. While the phase shift signal used in the algorithm is insensitive to the fluid media, the amplitude signal can show differences between different fluid media.

The durable portion 106 according to an embodiment of the invention contains an ambient temperature sensor that is useful for compensation of the sensor output. The temperature sensor is periodically monitored to ensure that the insulin is kept with the manufacturer's specified temperature range during use. Temperature tracking helps to ensure insulin viability and minimize the potential for insulin damage caused by exposure to temperature extremes. Additionally if the device detects that the pen 102 temperature is approaching either the lower or upper temperature limit, it can notify the user of this potential problem, enabling the user to prevent damage to the medication. Aside from exposure to temperature extremes, insulin can also be damaged over time by the cumulative exposure to temperatures that are minimally to moderately elevated, and the system can provide appropriate warnings to the patient in advance of a predetermined value for the cumulative temperature.

Embodiments of the invention preferably include an accelerometer 1514. This allows the device to detect excessive agitation of the pen 102 and can warn the user if the storage conditions are not appropriate to help maintain insulin viability. The temperature sensor and accelerometer can be used independently, as described above, or their information can be combined, and the cumulative values assessed against pre-programmed thresholds to identify the level of concern regarding the state of the insulin. The system can also track both temperature and agitation over time to predict the combined cumulative impact from these influences and provide the appropriate alerts to the patient.

Injections are delivered to specific areas or zones on the human body, due to the similarity in pharmacokinetics in these zones, that is, the rate of uptake of the drug into the patient's system. According to an exemplary embodiment of the present invention, the phone application sequentially recommends the ideal injection site, based on site rotation guidance, which if followed would reduce the likelihood of lypohypertrophy.

Alternately, with additional sensors such as a gyroscope and magnetometer added to the existing accelerometer, creating an inertial measurement unit (IMU), the device can be used to provide body tracking capabilities. With the accelerometer providing the relative magnitude of movement and the gyroscope providing directionality, an embodiment of the invention can track its location in a three dimensional space. The magnetometer provides correction to the other sensors based on magnetic fields detected. Given a set starting point such as the waist, the device according to this embodiment can detect approximate injection sites used for each injection. Pattern recognition of the motion immediately before a dose event can determine if single site injection is repeated or site rotation compliance is adhered to. The device can sense repeated injections to the same location and recommend injection site rotation in order to prevent lypohypertrophy from occurring. Assuming the user will use similar motions to move the pen to the injection site and deliver the dose, and that each transition to each specific zone on the body has uniqueness as measured by the gyroscope and accelerometer, then the system can be programmed to recognize to which zone the user is injecting, make site recommendations, and record the patterns of use/overuse for each site Embodiments of the invention can learn user injection habits including injection duration, dose sizes, injection times during the day, and so on. By tracking the normal injection duration times, embodiments of the invention can indirectly detect additional resistance to injection/flow. This additional injection resistance could be the result of lypohypertrophy at the injection site. The device can then recommend that the user rotates the injection site. Additional injection resistance could also be occlusion of flow within the needle or pen injector, which could prevent the user from receiving the intended dose. Dose information is relayed to the user, and can be flagged as consistent or abnormal, which will help identify dose errors.

Embodiments of the invention can track the remaining insulin in the pen by subtracting the dispensed injection volumes from the starting pen volume. The device can additionally alert the user when the pen is below a low volume threshold. If the remaining pen volume is below the typical dose volume that the user injects, the smart phone 102 application can communicate a recommendation to the user that the user carry an additional pen 102 to ensure adequate insulin volume for their next injection.

Embodiments of the invention can alert the patient to potential missed doses based on injection dose history. Over time the device can learn the patient injection habits, including typical injection durations for specific dose volumes. This data can be analyzed with various software, such as case based reasoning, or higher level insight engines to provide alerts, recommendations, and meaning to the patient.

Figure 19B:
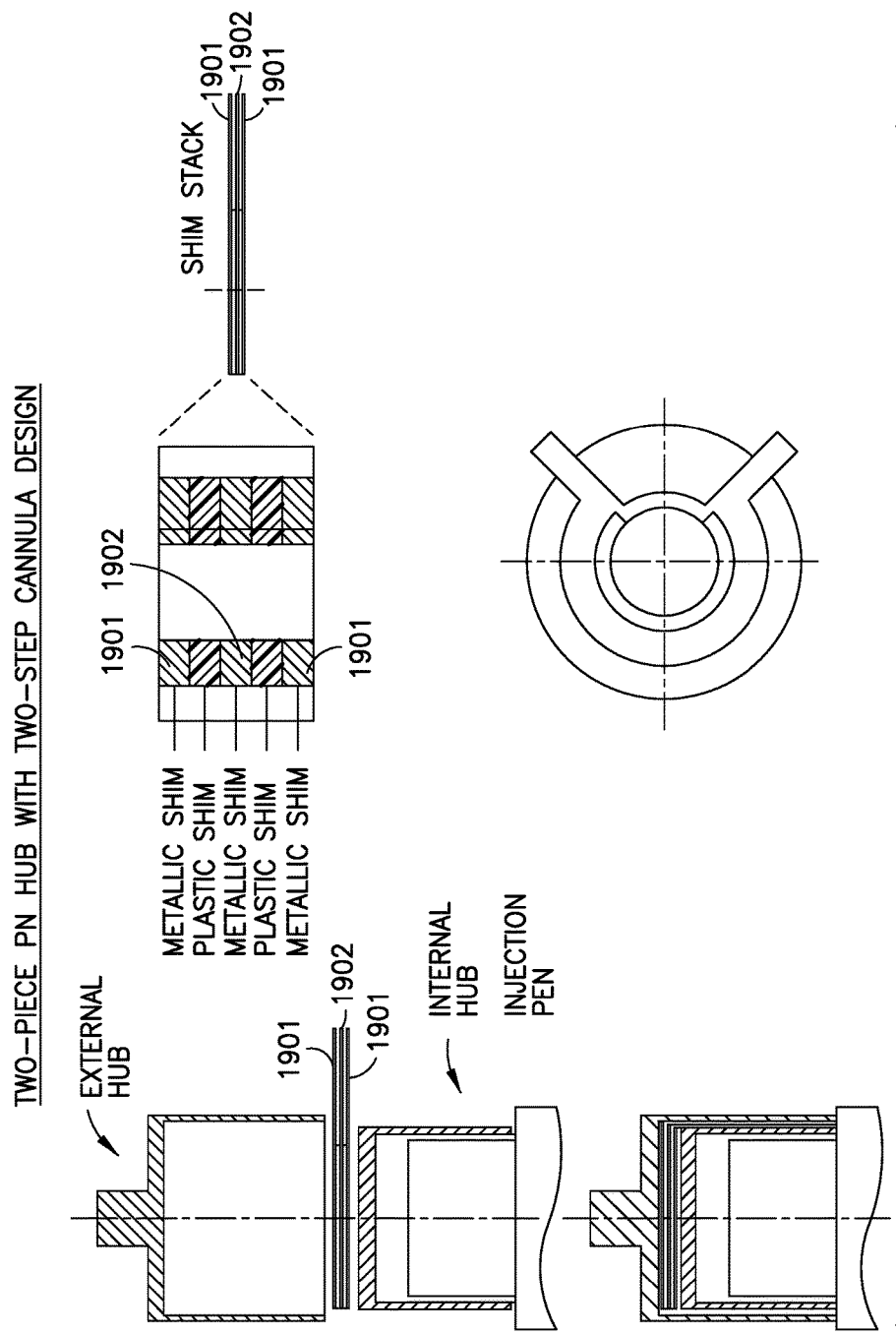

Although one embodiments of the invention described herein uses micro fabrication on a glass substrate, those of ordinary skill in the art will recognize that other embodiments could use larger scale fabrication techniques. One such embodiment consists of three conductive rings incorporated into a segment of cannula, as illustrated in FIGS. 19A and 19B. As illustrated, three rings 1901, 1902 function in a similar manner to the three elements of the TTOF chip described above. In this embodiment, the three rings would incorporate the flow sensor into the cannula. The cannula material preferably has a low thermal conductivity or alternately a thermal insulator material is used on both sides of the three rings. The three rings are preferably formed by stacking metallic and plastic shim material to form a laminate.

Polymer is a low cost, low thermal conductivity substrate that is a viable alternative to glass. Polymers typically have a thermal conductivity of 0.5 W/mK, which is lower than borosilicate glass (1.2 W/mK). There is ongoing development of flexible electronics whereby circuits and even simple transistors are printed or otherwise deposited onto polymeric substrates using roll-to-roll processing. However, a flexible sensor is not desirable since it will displace when subjected to up to 1 MPa of pressure in the flow channel, which may cause sensor drift and inaccuracy. This can be ameliorated by using a thicker than normal polymer substrate. Alternately, the polymer film can be laminated to a rigid material before singulation of the individual sensors.

As discussed above, there are specific characteristics of both the thermistors and the flow channel that need to be maintained to optimize the performance of the Thermal Time of Flight (TTOF) sensor. These include the cross sectional area of the thermistor trace; the length of the trace that is exposed to the drug or fluid; the height of the flow channel in relation to the spacing between thermistors; the "proudness" or positive positioning of the thermistors in relation to the adjacent surface of the flow channel; the design of the flow channel, including transition surfaces, and minimization of steps and burrs, to facilitate laminar flow throughout the range of velocity that is typical of insulin injection; and the repeatability of the dimensions, tolerances and cross-section of the thermistors and the positioning of the thermistors in relation to each other and in relation to the flow channel.

Traditionally these collective criteria could only be satisfied by a highly precise manufacturing process such as MEMS fabrication. However, for the context of placing thermistors within a cannula, conventional fabrication processes can be utilized to eliminate the need for a MEMS fabricated element, and additionally provide design alternatives with minimal loss in sensing performance that can enable integration into existing devices with minimal impact to the form factor. FIGS. 19A and 19B, discussed above, depict one such design in which a stack of laminations 1901, 1902, has been contained within a two-piece pen needle that would be used for drug delivery from an insulin injection pen. In this embodiment, the flow channel is cylindrical and the stack of laminations can be produced from traditional stamping processes, i.e. die cutting, to provide alternating layers of insulator, such as polymer, and conductor, such as metallic foil. The thickness of the polymer laminates would define the spacing between the thermistors, and the thickness of the metallic laminates would provide the exposed surface of the thermistor circuits that is in contact with the fluid. As described, these alternating layers can be produced individually, or from composite laminate structures, that is, a polymer and metallic laminate. To reduce the cross-section of the trace, the metallic layer could be either reduced after the laminated stack has been assembled by means of a secondary stamping operation, or for composite laminates, the metallic trace could be chemically etched in a process similar to photo-etching that is used to produce the electrical connections in electronic devices, such as lead frames used in semi-conductors. In another alternative embodiment, conductive material could be coated onto the polymer layer using vacuum deposition, such as the processes used to produce rolled capacitors. In another embodiment, the polymer layer could be replaced with aluminum, and the top and bottom surfaces of the aluminum layer could be oxidized to provide an insulating aluminum oxide layer.

Figure 21A:
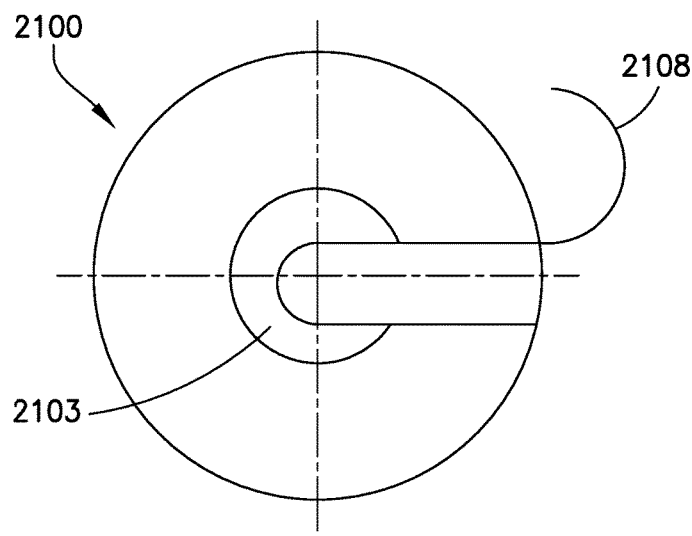
FIGS. 21A-21B illustrate a flexible substrate and etched sensor design according to an exemplary embodiment of the invention.
Figure 21B:
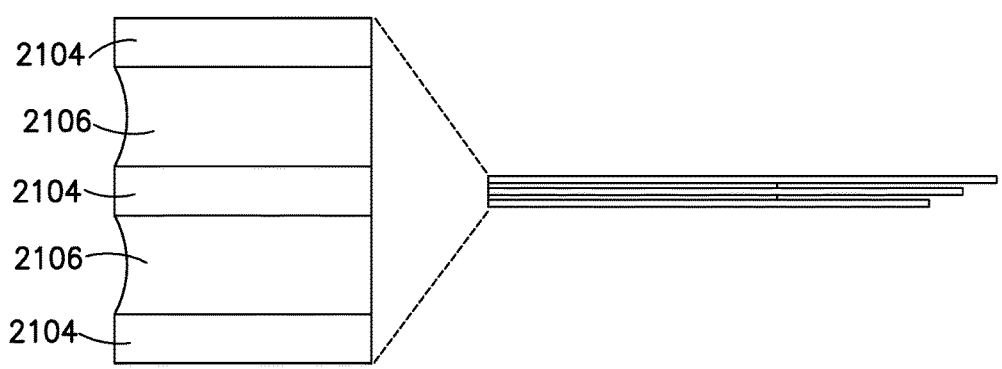
Figure 22A:
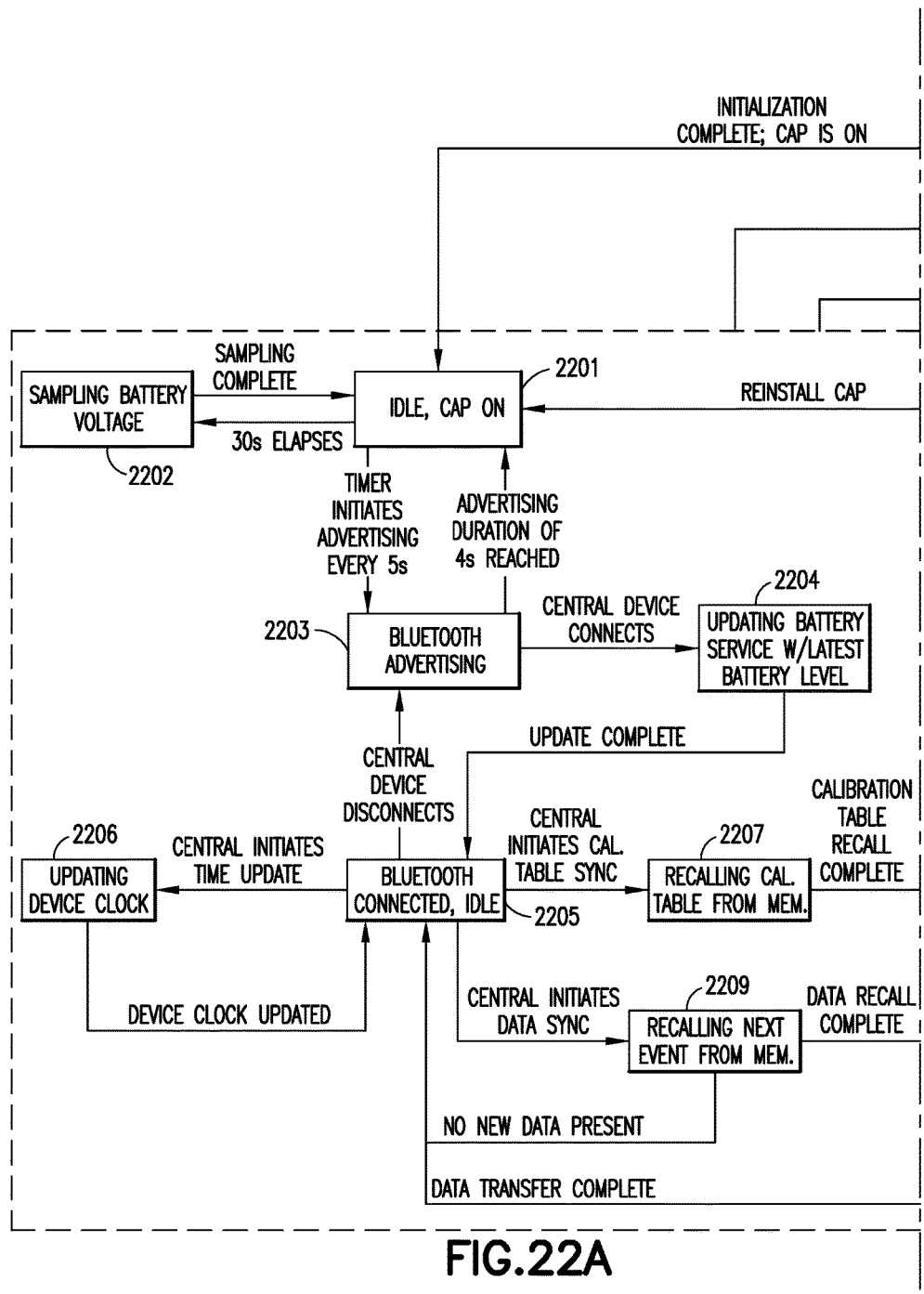
FIG. 22A-22B is a state transition diagram describing operation of an exemplary embodiment of the invention.
Figures 22, 22B:
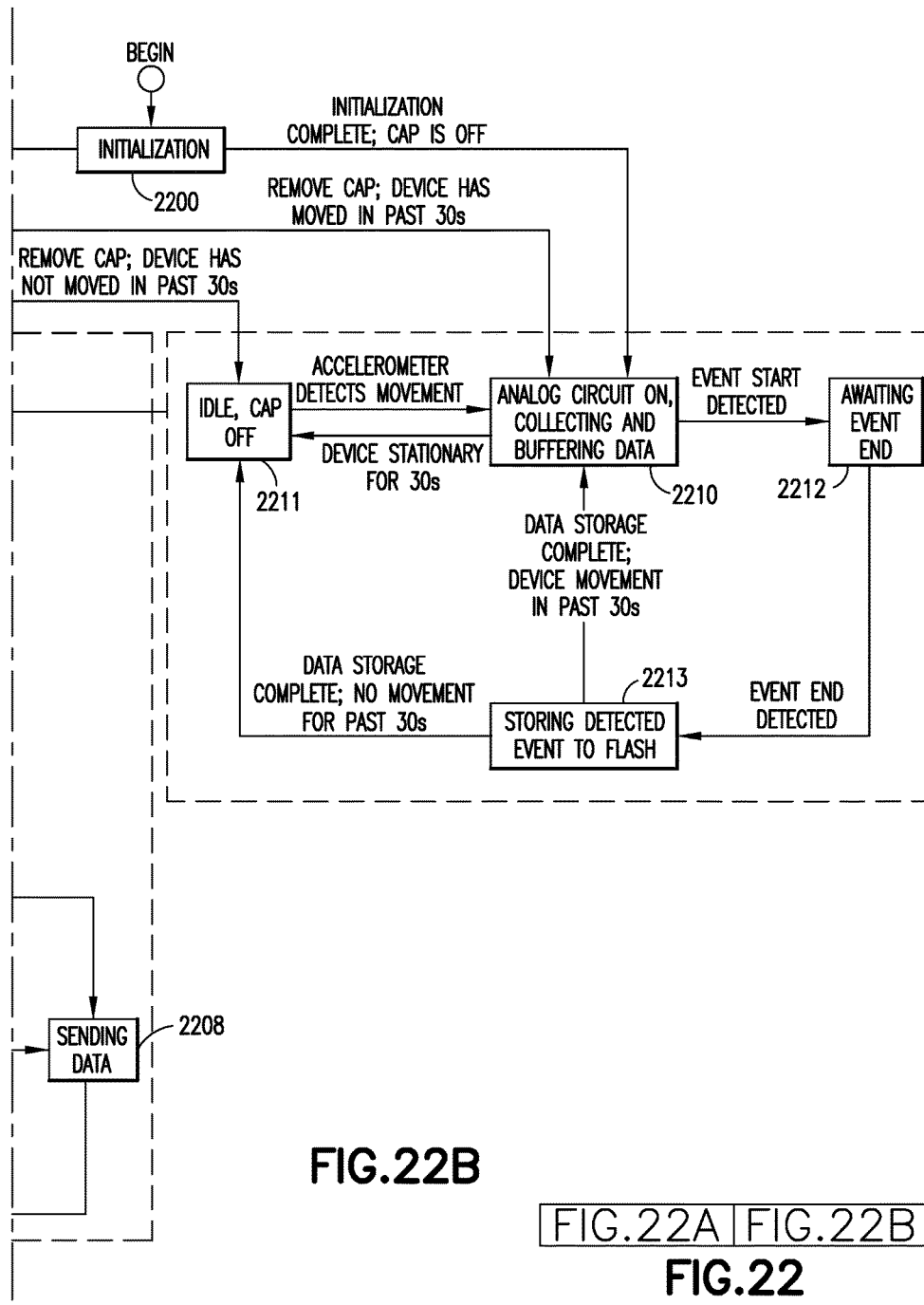

As illustrated in FIGS. 21A and 21B, following stamping and assembly of the laminated stack, a chemical etch process is used to undermine the aluminum 2106, thereby increasing the proudness of the exposed surfaces of the non-aluminum, metallic laminations 2104 in relation to the adjacent surfaces in the laminated stack and flow channel. FIG. 21A illustrates a top view of the laminated stack 2100 and flow channel formed therein 2102. FIG. 21B illustrates a cross section of a laminated structure formed from alternating aluminum 2106 and non-aluminum metallic laminations 2104, in which the exposed surface of the aluminum 2106 is etched or undermined. In another embodiment shown in FIG. 21A, the thermistors are printed onto a flexible substrate 2108 and wrapped around a convex shaped insert that when assembled to the molded housing of a pen needle would create a C-shaped cross-section 2103 in the sensing zone of the flow channel. The convex shaped insert would incorporate the pre and post surfaces to transition the cylindrical cross section to a C-shaped cross section and then back to a cylindrical cross section. This embodiment enables the relationship between the channel height and the distance between thermistors to be more closely matched. To provide electrical connections on the exterior of the pen needle, the conductive traces on the flexible substrate 2108 can be either (1) wrapped around the outer diameter of the inner pen needle hub, or (2) folded to extend to the base of the inner pen needle hub, and the assembly of the external pen needle hub would provide either (1) over-molded conductive pads and connection points located around the outer diameter of the external pen needle hub or (2) connection points located at the base of the assembled pen needle, respectively.

In another embodiment, a thin wire, such as 0.001 inch, is wrapped around the convex insert, such that each wrap is spaced at a distance equivalent to the MEMS fabricated thermistor spacing. The wires are terminated on the back side of the insert to enable individual connection to the PCBA located in the durable element of the system. The use of wire is advantageous, because of the accuracy of the wire diameter and the ability to plate or coat the Pt and passivation layers onto the outer diameter of the wire using continuous coating processes. To balance the mechanical properties of the wire and the need to minimize the cross-section of the heater and sensor elements, the base wire can be a polymer or other thermal insulating material. Alternately, a very thin Platinum Wollaston wire, available commercially with diameters in the 1 micron range, may be used.

Micro-fabrication processes, as also known as MEMS fabrication, produce thermistor traces to cross-sectional dimensions and tolerance within sub-micron accuracy. This is highly beneficial to the design and operation of the sensor, i.e. resistance variation from trace to trace is extremely small. Macro fabrication, which processes include: stamping, chemical etching, rolling and calendaring mills, laminating and printing, have significantly higher dimensional/tolerance inaccuracies, e.g. the best case dimensional accuracy and tolerance for a trace produced from the macro methods identified could be +/−0.0005 inch for cross-section and +/−0.0001 inch for thickness. Alternately, electronics printing or methods like nano imprint lithography can be used to attain very fine resolution, far better than most macro fabrication methods.

Maintaining tighter dimensions and tolerance for all of the mechanical, e.g. flow channel, and electrical, e.g. thermistor trace, components in the sensor enables greater sensing accuracy, and as the fabrication errors for each element are reduced to approach zero, the sensing accuracy will also be improved proportionally. Although the ultimate goal is to reduce or eliminate all system error and noise, there are many applications where size, form factor, cost and other considerations could be satisfied with less accurate sensor elements produced by macro fabrication methods. For example, a highly scalable combination of macro fabrication processes would involve the use of ink jet printing or Physical Vapor Deposition (PVD) to apply the thermistor traces onto a flexible substrate and wrapping that substrate around a convex insert to suspend the traces in the center of the cannula.

A hybrid TTOF MEMS sensor according to an exemplary embodiment of the invention preferably has micron scale features. In one embodiment, the line width of the Platinum thermistors (heating and sensing elements) is 4 microns. It is challenging to replicate these features using a roll-to-roll printing process on a flexible (polymer) substrate since the resolution is typically in the range 20-30 microns at best for both ink jet and non-serial methods like gravure, flexography and offset printing. However, it is feasible to scale up the sensor dimensions with larger heater and sensor element widths and lengths, and larger separation between the elements. Conventionally microfabricated hybrid TTOF sensor prototypes with larger sensor to heater separation, for example 300 to 400 microns, demonstrated adequate amplitude and phase signal strength when powered in the standard 5-30 mW range. On the other hand, 2 micron resolution using gravure printing has recently been demonstrated by Subramian et al. at the University of California at Berkeley. This suggests that the same dimensions as the current microfabricated structure will be attainable using printing in the foreseeable future. Registration is also challenging for roll-to-roll processing but for this sensor design the layer-to-layer alignment is not critical with several 10 s of micron registration accuracy being adequate. Another challenge with roll-to-roll printing is that the thermistor material (e.g. Platinum or Polysilicon) has to be formulated as an ink and cured, but there are many vendors who are skilled in the art of formulating such inks.

An alternative approach is to use microfabrication techniques, namely lithography and vapor deposition, combined with roll-to-roll processing. Nanoimprint Lithography (NIL) has been developed since approximately 1995 as a simple and effective method to produce nanoscale features. NIL is a process where nanoscale structures on a mold (or template) are transferred onto a substrate coated with thermoplastic or ultraviolet (UV) curing resins by making contact with the substrate while being heated or exposed to UV light, respectively. There are still technical challenges for roll-to-roll NIL and it is still mostly in the academic sphere of development. Attaining high speed is particularly challenging while allowing enough time for the imprint. Nevertheless, roll-to-roll NIL is a possible future method of fabricating the hybrid TTOF sensor.

Soft lithography, especially Microcontact Printing (MCP), is another process that can be used for roll-to-roll processing. It is an alternative to NIL, having an inherent advantage in terms of speed since it does not have to make an actual imprint into a resin. The disadvantage is that it requires inking as in any printing process. A research group at The Chinese University of Hong Kong developed a roll-to-roll MCP process to fabricate both high quality nano- and single digit micron-resolution patterns of both gold and silver, using a flexure mechanism based roll-to-roll machine. The speed was modest at 0.02 cm/s.

Another alternative embodiment of the invention is to directly incorporate the MEMS flow sensor into the pen needle. This makes the flow sensor disposable after single use, inasmuch as the pen needle is discarded after an injection, which also means that the sensor is preferably fabricated at low cost. Economies of scale reduce cost when a large volume of miniaturized sensors are fabricated from 300 mm wafers. Miniaturization, enabled by the via design discussed above, allows for a die size in the 1.0-1.2 mm square range. An exemplary calculation shows that a single 300 mm wafer yields nearly 40,000 1.2 mm square sensors. The sensor chips can be manufactured using a CMOS compatible process at a state-of-the-art 300 mm semiconductor fabrication plant. CMOS compatibility means that the heating and sensor elements (thermistors) are manufactured using doped Polysilicon rather than Platinum. A single use application does not require the corrosion resistance provided by Platinum, and the use of Polysilicon for thermal flow sensors is well established in the scientific literature.

What is claimed is:
1. A flow sensor system comprising:
 a durable portion comprising
  an outer housing having a first opening to receive an injection device, and a second opening at an opposite end to receive a semi-disposable portion;
  a durable portion electrical connector;
  a memory;
  a battery;
  a processor for receiving and processing signals received from the semi-disposable portion, and for driving the wireless transceiver to send and receive communication signals from the remote device;
a semi-disposable portion comprising:
a first end having a cannula adapted to pierce a septum of the injection device and a female thread adapted to engage a male thread feature of the injection device;
a second end opposite the first end having a male pen needle thread and septum adapted to receive a pen needle;
a printed circuit board having mounted thereon a flow sensor chip;
a manifold in fluid communication with the cannula and the septum, the manifold comprising a continuous flow channel extending from the first end cannula to a chamber adjacent the second end septum, the flow channel comprising an opening to receive a sensor; and
a semi-disposable portion electrical connector for electrical connection to the durable portion electrical connector;
wherein the flow sensor chip comprises a sensing surface adapted to be received in the flow channel opening and exposed within the flow channel; the sensor surface having a heating element and at least one sensing element downstream of the heating element.

2. The flow sensor system of claim 1, wherein the semi-disposable portion further comprises a deformable locking element that deforms to permit the semi-disposable portion to be installed into the durable portion, and locks the semi-disposable portion into the durable portion once fully installed.

3. The flow sensor system of claim 1, wherein the semi-disposable portion further comprises an alignment feature to align the semi-disposable portion with the durable portion.

4. The flow sensor system of claim 1, wherein the flow sensing chip further comprises a second sensing element upstream of the heating element.

5. The flow sensor system of claim 4, wherein the first sensing element and the second sensing element are equidistant from the heating element.

6. The flow sensor system of claim 1, wherein the semi-disposable portion comprises an alignment feature to align the semi-disposable portion to the durable portion, and a snap flexure to lock the semi-disposable portion within the durable portion once inserted.

7. The flow sensor system of claim 1, wherein the manifold has a first portion with a first cross sectional area, and a second portion with a second cross sectional area, and wherein the flow sensor chip is exposed to the first manifold portion, and a second sensor chip is exposed to the second manifold portion.

8. The flow sensor system of claim 4, wherein the flow sensing chip further comprises a secondary pair of sensing elements spaced equidistantly from the heating element at a second distance upstream and downstream of the heating element, the second distance being different than the distance from the heating element to the at least one sensing element and the second sensing element.

9. The flow sensor system of claim 1, wherein the heating element and the sensing element are electrically connected to the electrical connector.

10. The flow sensor system of claim 9, wherein the electrical connection is made by wire bonding on a conductive pad that is adjacent to and connected to the sensing surface.

11. The flow sensor system of claim 9, wherein the electrical connection is made by conductive material within a plurality of vias providing electrical connection from the sensing surface to an opposite surface of the sensing chip.

12. The flow sensor system of claim 1, wherein the electrical connector of the semi-disposable portion is oriented such that the semi-disposable portion becomes electrically connected to the durable portion when the first end cannula pierces the septum of the injection device.

13. The flow sensor system of claim 1, wherein the durable portion further comprises a wireless transceiver for communicating with a remote device.

14. A method of measuring a dose of medicament delivered through a cannula with a sensor comprising a heating element and a first pair of sensing elements comprising an upstream sensing element and a downstream sensing element, the pair of sensing elements spaced at a first offset distance equidistantly upstream and downstream of the heating element, comprising the steps of:
generating a heating signal with the heating element;
detecting the beginning of medicament flow by sensing a difference in signals received from the upstream and downstream sensing elements;
periodically sampling the upstream and downstream sensing elements to measure instantaneous flow rates;
determining an end of medicament flow;
determining a dose volume based on a plurality of sampled instantaneous flow rates; and
storing the determined dose volume in a memory unit.

15. The method of claim 14, wherein the heating signal is time varying.

16. The method of claim 14, wherein the determining a dose volume step comprising integrating substantially all of the sampled instantaneous flow rates over the duration of the medicament flow.

17. The method of claim 14, wherein the determining a dose volume step comprises matching a set of sampled flow rates to one of a plurality of flow rate templates stored in a table of a memory, each template being associated with a different dose volume.

18. The method of claim 14, wherein the sensor comprises a second pair of upstream and downstream sensing elements spaced at a second offset distance equidistantly upstream and downstream of the heating element, wherein the second offset distance is greater than the first offset distance, the method further comprising the step of:
periodically sampling the first pair of sensing elements if the flow rate is determined to be in a first range, and sampling the second pair of sensing elements if the flow rate is determined to be in a second range.

19. The method of claim 14, wherein the sampling step comprises measuring a relative amplitude and phase based on the heating signal at each of the upstream and downstream sensing elements.

20. The method of claim 19, wherein instantaneous flow rates are determined based on a table lookup of amplitude and phase values.

21. A medicament flow sensor comprising:
a manifold comprising a flow channel extending between an inlet and an outlet;
a sensor comprising a sensor face having:
a heating element; and
a first pair of sensing elements spaced equidistantly upstream and downstream of the heating element;
wherein the sensor face is exposed to fluid in the flow channel, and is substantially flush with or proud of a manifold surface of the flow channel.

22. The medicament flow sensor of claim 21, wherein the flow channel has a substantially rectangular cross section of known area adjacent to the sensor face.

23. The medicament flow sensor of claim 22, wherein the flow channel connects to a round cannula at the inlet and a round cannula at the outlet, and the flow channel comprises smooth transitions between portions of the flow channel with round cross section at the inlet and outlet, and the substantially rectangular cross section at the sensor face.

24. The medicament flow sensor of claim 21, wherein the volume of the flow channel is less than 30 microliters.

25. The medicament flow sensor of claim 21, further comprising a second sensor comprising a sensor face having a heating element and a pair of sensing elements spaced equidistantly upstream and downstream of the heating element, the second sensor located in a second portion of the flow channel having a different cross sectional area than the portion of the flow channel adjacent to the first sensor.

26. The medicament flow sensor of claim 21, wherein the sensor face is formed on a rigid substrate.

27. The medicament flow sensor of claim 21, wherein the sensor face is formed on a glass substrate.

28. The medicament flow sensor of claim 21, wherein the sensor face is formed on a rigid substrate having a thermal conductivity less than 2 W/mK.

29. The medicament flow sensor of claim 21, wherein the sensor face is formed of a polymer substrate having a thickness sufficient to resist deflection due to fluid pressure imparted by medicament within the flow channel during a dosing event.

* * * * *